US012161389B2

(12) United States Patent
Norton et al.

(10) Patent No.: US 12,161,389 B2
(45) Date of Patent: Dec. 10, 2024

(54) ARTHROSCOPIC DEVICES AND METHODS

(71) Applicant: Relign Corporation, Campbell, CA (US)

(72) Inventors: Jeffrey Norton, Emerald Hills, CA (US); Evan Nessim, Los Gatos, CA (US); Aaron Germain, San Jose, CA (US); Michael D Walker, San Francisco, CA (US)

(73) Assignee: Relign Corporation, Campbell, CA (US)

( * ) Notice: Subject to any disclaimer, the term of this patent is extended or adjusted under 35 U.S.C. 154(b) by 294 days.

(21) Appl. No.: 17/376,650

(22) Filed: Jul. 15, 2021

(65) Prior Publication Data

US 2022/0015821 A1 Jan. 20, 2022

Related U.S. Application Data

(60) Provisional application No. 63/052,330, filed on Jul. 15, 2020.

(51) Int. Cl.
*A61B 18/14* (2006.01)
*A61B 18/00* (2006.01)

(52) U.S. Cl.
CPC .. *A61B 18/148* (2013.01); *A61B 2018/00202* (2013.01); *A61B 2018/00577* (2013.01);
(Continued)

(58) Field of Classification Search
CPC ........ A61B 18/148; A61B 2018/00202; A61B 2018/00577; A61B 2018/00607;
(Continued)

(56) References Cited

U.S. PATENT DOCUMENTS 6,368,336 B1 * 4/2002 Ronvig ..................... A61C 3/02
606/180
9,855,675 B1 1/2018 Germain et al.
(Continued)

FOREIGN PATENT DOCUMENTS

WO WO-2021126852 A1 6/2021

OTHER PUBLICATIONS

"European Application Serial No. 21185946.7, Extended European Search Report mailed Dec. 1, 2021", 7 pgs.
(Continued)

*Primary Examiner* — Linda C Dvorak
*Assistant Examiner* — Lindsay Regan Lancaster
(74) *Attorney, Agent, or Firm* — SCHWEGMAN LUNDBERG & WOESSNER, P.A.

(57) ABSTRACT

An arthroscopic cutter according to one embodiment of the present disclosure includes an elongated outer sleeve that extends about a longitudinal axis with an interior bore having an open distal end. An inner sleeve is rotatable in the interior bore in the outer sleeve. The inner sleeve carries a distal housing having a longitudinal metal member and a longitudinal ceramic member that respectively form longitudinal-extending sides of the housing around an inner channel that communicates with a negative pressure source. The arthroscopic cutter also includes an electrode that is disposed in an outer surface of the longitudinal ceramic member.

20 Claims, 31 Drawing Sheets

(52) U.S. Cl.
CPC .............. *A61B 2018/00607* (2013.01); *A61B 2018/147* (2013.01)

(58) Field of Classification Search
CPC .......... A61B 2018/147; A61B 18/1233; A61B 18/1442; A61B 2018/00196; A61B 2018/00601; A61B 2018/00898; A61B 2018/1452; A61B 2018/1497; A61B 2017/0088; A61B 2018/00208; A61B 2018/00565; A61B 2018/00589; A61B 2018/00708; A61B 2018/1472; A61B 2018/162; A61B 2090/067; A61B 2218/002; A61B 2218/007; A61B 17/32002

See application file for complete search history.

(56) References Cited

U.S. PATENT DOCUMENTS

| | | |
|---|---|---|
| 10,022,140 B2 | 7/2018 | Germain et al. |
| 10,052,149 B2 | 8/2018 | Germain et al. |
| 10,595,889 B2 | 3/2020 | Germain et al. |
| 2013/0103021 A1* | 4/2013 | Germain .......... A61B 17/32002 606/119 |
| 2013/0331833 A1* | 12/2013 | Bloom ............. A61B 17/32002 606/45 |
| 2014/0336643 A1* | 11/2014 | Orczy-Timko ...... A61B 18/149 606/45 |
| 2017/0224368 A1* | 8/2017 | Germain ............ A61B 17/3205 |
| 2017/0258519 A1 | 9/2017 | Germain et al. |
| 2018/0263649 A1* | 9/2018 | Germain ............ A61B 18/148 |
| 2019/0038305 A1* | 2/2019 | Smith ................ A61B 17/1659 |
| 2019/0059983 A1* | 2/2019 | Germain ........... A61B 17/1606 |
| 2019/0328417 A1 | 10/2019 | Germain |
| 2022/0160425 A1* | 5/2022 | Doll ...................... A61B 18/16 |

OTHER PUBLICATIONS

"European Application Serial No. 21185946.7, Response filed Jul. 19, 2022 to Extended European Search Report mailed Dec. 1, 2021", 14 pgs.

* cited by examiner

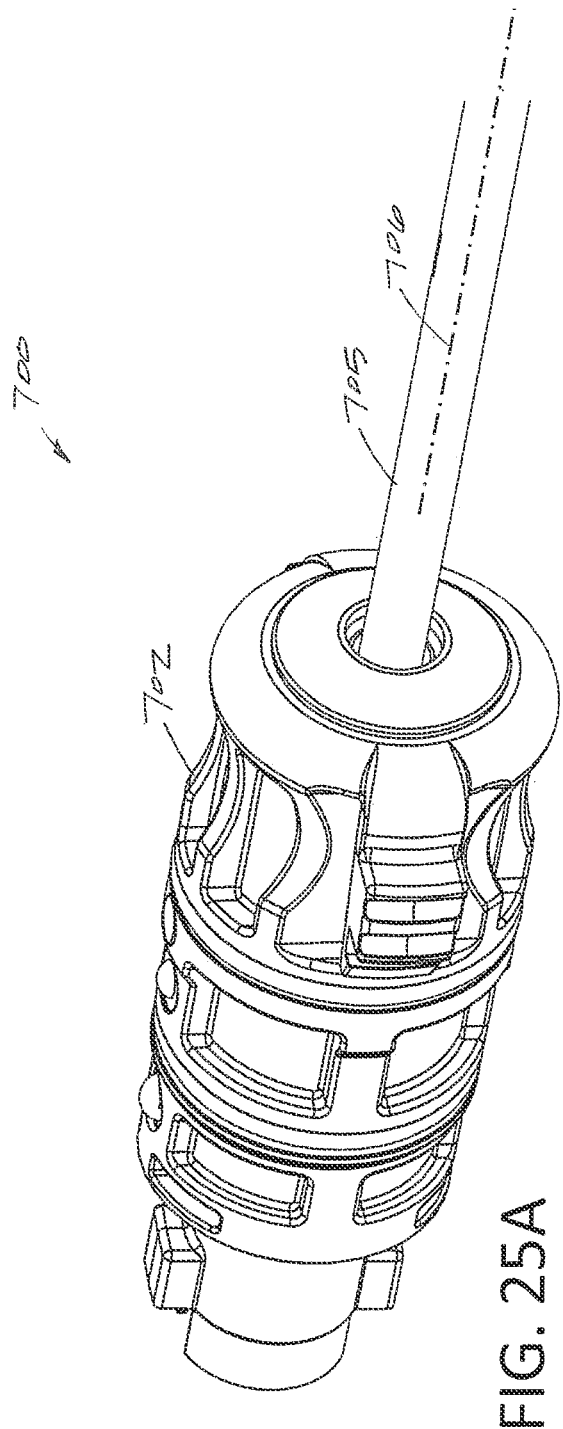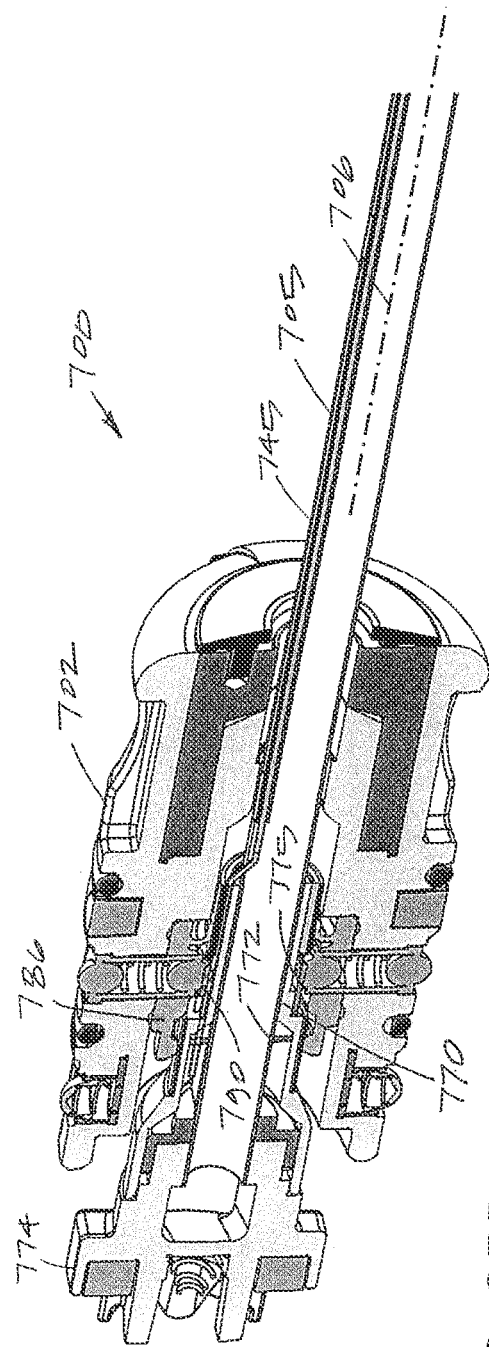
FIG. 25A
FIG. 25B

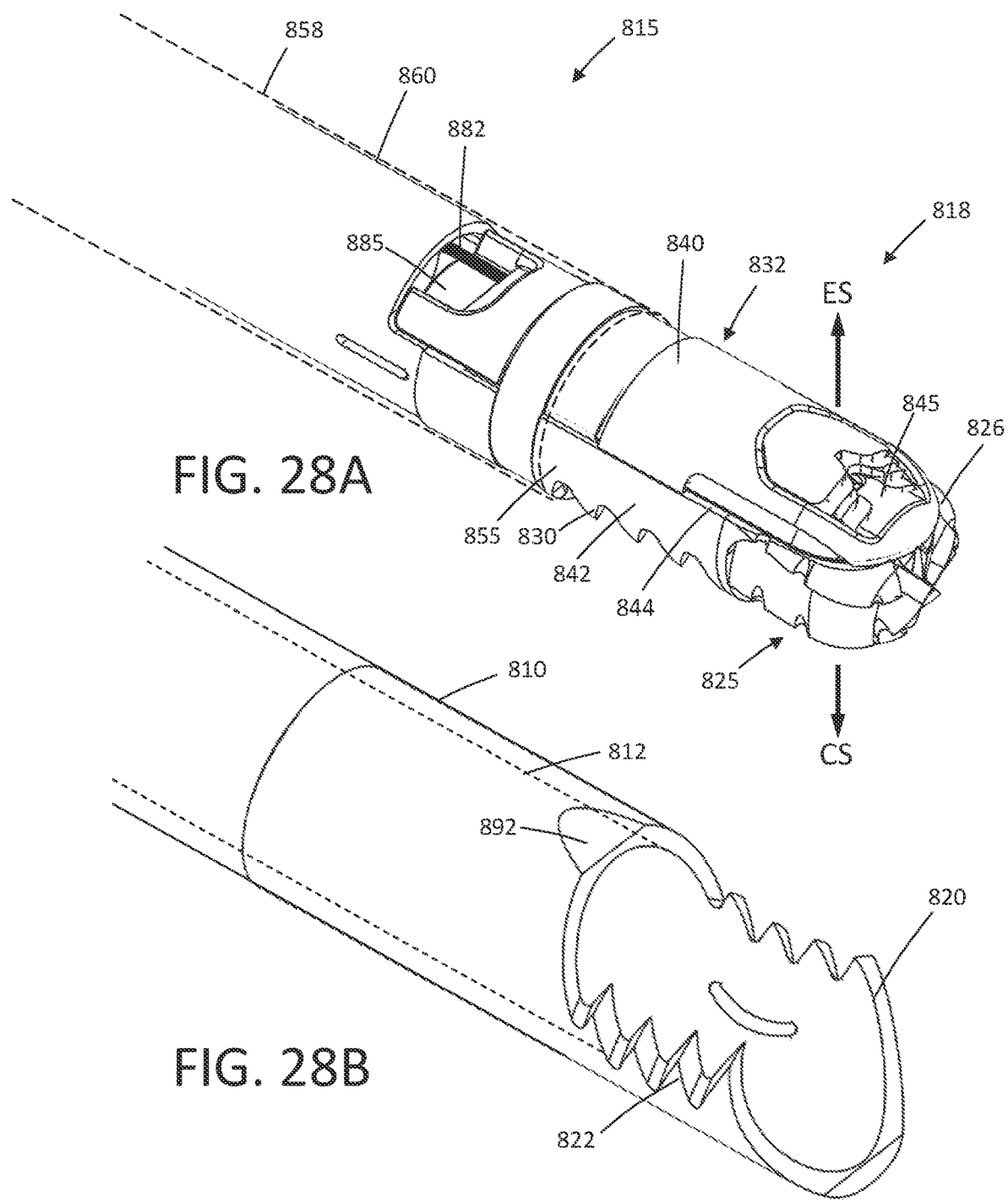

ARTHROSCOPIC DEVICES AND METHODS

CLAIM OF PRIORITY

This application claims the benefit of U.S. Provisional Patent Application Ser. No. 63/052,330, filed on Jul. 15, 2020, the benefit of priority of which is claimed hereby, and which is incorporated by reference herein in its entirety.

BACKGROUND OF THE INVENTION

1. Field of the Invention

This invention relates to a medical system that includes variations of motor-driven arthroscopic cutters or shavers that are configured for both mechanical cutting and electrosurgical cutting, as well as ablation and coagulation procedures.

2. Description of the Background Art

In endoscopic and other surgical procedures including subacromial decompression, anterior cruciate ligament reconstruction involving notchplasty, and arthroscopic resection of the acromioclavicular joint, there is a need for cutting and removal of bone and soft tissue. Currently, surgeons use arthroscopic shavers and burrs having rotational cutting surfaces to remove hard tissue in such procedures.

To promote efficiency, endoscopic tool systems including a reusable handpiece and a selection of interchangeable tool probes having different working ends have been proposed. Such working ends may each have two or more functionalities, such as soft tissue removal and hard tissue resection, so such tools systems can provide dozens of specific functionalities, providing great flexibility.

While a significant advantage, the need for one tool system to accommodate such flexibility is a challenge. In particular, it is necessary that the handpiece and control unit for the system be provided with correct information on the identity of the tool probe that has been attached as well as the operational parameters of the tool probe during use.

It is therefore an object of the present invention to provide improved surgical systems and methods for their use, such as improved arthroscopic tissue cutting and removal system wherein a motor-driven electrosurgical device is provided for cutting and removing bone or soft tissue from a joint or other site. It is a further object invention to provide improved systems and methods for device identification, monitoring, and control, such as controlled operational stopping and starting of motor-driven components in default positions. At least some of these objectives will be met by the inventions described herein.

SUMMARY OF THE INVENTION

The present invention provides improved apparatus and methods for identifying and controlling working components, such as motor-driven and other powered components, of surgical systems, particularly for arthroscopic and other surgical systems including (1) handpieces having motor drive units and (2) probes which are selectively and removably attached to the handpieces. In exemplary embodiments, the present invention provides methods and systems which rely on magnets and magnetic sensors for providing information to system controllers both in a static mode, where a laparoscopic or other tool is not being driven, and in a dynamic mode, where the tool is being driven by the motor drive. In particular embodiments, the magnets are permanent magnets having North poles and South poles, where the magnets are typically mounted on or otherwise attached or coupled to components of a detachable probe forming part of an arthroscopic system, and the sensors are Hall sensors which are in the handpiece of the arthroscopic system. By using multiple magnets and multiple sensors, different types of information can be provided to the system controller, such as identification of the tool in the detachable probe, operating characteristics of the probe, system calibration information, and the like. While the exemplary embodiments of present invention typically rely on magnetic sensors, static and dynamic data acquisition from the tool probe to the associated controller and be accomplished with other sensors as well, such as optical sensors which are able to read information in both a static mode and in a dynamic mode.

In a first aspect of the present invention, an arthroscopic system comprises a handpiece and a probe. The handpiece includes a motor drive, and the probe has a proximal hub and an elongate shaft which extends about a longitudinal axis to a working end of the probe. The hub is configured for detachably coupling to the handpiece, and the motor drive is configured to couple to a rotating drive coupling in the hub when the hub is coupled to the handpiece. A first magnetic component is carried by the hub, and a second magnetic component is coupled to rotate with the rotating drive coupling.

In specific aspects, the hub may be configured for detachable coupling to the handpiece in opposing rotational orientations, such as an orientation where a working end of the probe is facing upwardly and a second orientation where the working end of the probe is facing downwardly relative to the handpiece. In such embodiments, the first magnetic component may comprise first and second independent magnets, typically permanent magnets have North poles and South poles, disposed in or on opposing sides of the hub and spaced outwardly from the longitudinal axis. The first and second independent magnets of the first magnetic component will typically have a "polar orientation," for example the North poles will be oriented in opposite directions relative to said axis. Typically, though not necessarily, the first and second independent magnets may have similar magnetic field strengths. In such embodiments, the handpiece may further comprise a first sensor configured for "statically" sensing a magnetic field of the first or second independent magnets when located adjacent the first sensor. By "statically" sensing, it is meant that the magnets do not need to be moving relative to the sensor. The sensor will thus be able to generate a signal indicating whether the working end is in its upward-facing orientation or its downward-facing orientation. The first sensor may be further configured for generating a probe identification signal based on the magnetic field strength (or other magnetic characteristic) which correlates a probe type with different magnetic field strengths, typically by using a look-up table maintained in an associated controller.

In still other embodiments, the second magnetic component comprises third and fourth independent magnets disposed in or on opposing sides of the rotating drive coupling. The third and fourth independent magnets of the second magnetic component will typically have North poles in opposing orientations relative to said axis, usually in a manner similar to the first and second independent magnets. The handpiece will further comprise a second sensor configured for sensing a magnetic field of the third or fourth independent magnets as the magnet comes into proximity to the second sensor. In this way, the second sensor can dynamically sense and generate a signal indicating a rotational parameter of the rotating drive coupling. For example, the rotational parameter may comprise a rotational position of the drive coupling. Alternatively or additionally, the rotational parameter may comprise a rotational speed of the drive coupling based on the rotational positioning over a time interval.

These arthroscopic and other surgical systems may be further configured for determining orientation of the motor-driven component so that the working end can be stopped in a desired position. For example, the second magnetic component carried by the drive coupling may be in a fixed predetermined rotational relationship to a motor-driven component in the working end. In this way, a rotational positioning of the component in the working end van be controlled based on the rotational position of the drive coupling.

Such systems of the present invention may further comprise a controller configured to receive the signals generated by the sensors and provide monitoring and control of the endoscopic or other surgical tool based on the received signals. For example, by receiving signals generated by the first sensor within the hub, at least one of probe-orientation and probe identification can be determined. Similarly, by receiving signals generated by the second sensor within the hub, the controller may be configured to monitor and/or control the motor speed and other operational characteristics.

In a second aspect of the present invention, a method for performing an arthroscopic procedure comprises providing a system including a handpiece with a sensor. The system further comprises a probe having a proximal hub, a longitudinal axis, and a working end. The hub typically carries first and second magnets having North and South poles. The hub is selectively coupled to the handpiece with the working end of the probe in either an upward orientation or a downward orientation. The first magnet is located proximately to sensor when the working end is in the upward orientation, and the second magnet is located proximately to sensor when the working end is in the down orientation. In this way, an upward orientation or a downward orientation of the working end can be determined based on whether a North pole or a South pole of the magnet is proximate to the sensor. Such orientational information is used for a variety of purposes, including selecting a controller algorithm for operating the probe based on the identified orientation of the working end.

In a third aspect of the present invention, an arthroscopic or other surgical method comprises providing a system including a handpiece with a sensor. The system further comprises a probe with a proximal hub, a longitudinal axis, and a working end. The hub will carry first and second magnets of similar strengths and having North and South poles. The hub is coupled to the handpiece, and a magnetic strength of either (or both) of the magnets is sensed using a sensor in the handpiece to identify the probe type based on the sensed magnetic strength. Identification of the probe type is useful for a variety of purposes, including allowing selection of a control algorithm (to be used by a controller coupled to probe and sensors) to control the working end of the tool based on the identified probe type.

In a fourth aspect, an arthroscopic or other surgical procedure comprises providing a system including a handpiece with a motor drive. The system further comprises a probe having a proximal hub, a longitudinal axis, a rotating drive coupling, and a working end. The rotating drive coupling typically carries first and second magnets having North and South poles where each pole is positioned in a different orientation relative to the axis. The hub is attached to the handpiece to couple the motor drive to the rotating drive coupling in the hub. The rotating drive coupling actuates a motor-driven or other component in the working end, e.g. the motor drive may be activated to rotate the drive coupling and actuate the motor-driven component. A varying magnetic parameter is sensed with a sensor in the handpiece as the drive coupling rotates in order to generate sensor signals. A rotational position of the drive coupling can thus be determined, and the corresponding positions of the motor-driven component calculated using a positioning algorithm responsive to the sensor signals. The motor drive can be selectively deactivated at a desired rotational position based on the positional information which has been thus determined. After deactivating the motor drive, the system can dynamically brake the motor drive to thereby stop rotation of the drive coupling and stop movement of the motor-driven component in a selective stop position in a highly accurate manner.

In a fifth aspect of the present invention, an arthroscopic procedure comprises providing a system including a handpiece with a motor drive. The system further comprises a probe with a proximal hub and an elongate shaft extending about an axis to a working end. The hub is configured for detachable coupling to the handpiece, and the motor drive is configured to couple to a rotating drive coupling in the hub. The drive coupling, in turn, carries first and second magnets with North and South poles positioned in different orientations relative to the axis. The hub is coupled to the handpiece, and the motor drive is activated to rotate the drive coupling and magnets through an arc of at least 180°. A varying strength of each magnet is then sensed with a sensor in the handpiece as the drive coupling rotates. A rotational position of the drive coupling responsive to the varying strength of each magnet can be calibrated in order to increase accuracy in subsequent calculation of the sensed strengths of the magnets.

In a sixth aspect of the present invention, an arthroscopic procedure comprises providing a handpiece with a motor drive. The system further comprises a probe having a proximal hub and an elongate shaft extending about a longitudinal axis to a working end having a motor-driven component. The motor-driven component includes a radio frequency (RF) electrode, and a hub is configured for detachable coupling to the handpiece. The motor drive is configured to couple to a rotating drive in the coupling of the hub, and the rotating drive coupling is configured to carry first and second magnets with North and South poles positioned in different orientations relative to the axis. The hub is coupled to the handpiece, and the drive coupling and motor-driven component are positioned in a selected stop position. The RF electrode is typically exposed in the selected stop position and can be introduced to a target site to engage or interface with tissue. RF current is then delivered to the RF electrode, and a positioning algorithm responsive to sensor signals continuously monitors the rotational position of the drive coupling and the corresponding position of the motor-driven component and the RF electrode while RF current is being delivered. Such position monitoring is useful because it allows the positioning algorithm to sense a rotation or rotational deviation greater than a predetermined amount, in which case the delivery of RF current to the RF electrode can be terminated. Additionally or alternatively, the positioning algorithm can further activate or adjust the motor drive to return the RF electrode back to a selected or desired stop position.

In a seventh aspect, an arthroscopic procedure comprises providing a handpiece with a motor drive and a probe with a proximal hub. An elongate shaft of the hub extends about an axis to a working end, and a motor driven component in the working end includes an RF electrode. The hub is configured for detachably coupling to the handpiece, and the motor drive is configured to couple to a rotating drive coupling in the hub. The rotating drive carries first and second magnets with North and South poles having different orientations relative to the axis. The hub is coupled to the handpiece, and the drive coupling and motor-driven component may be positioned in a selected stop position. The RF electrode may be engaged against a target issue surface or interface, and an RF current may be delivered to the RF electrode. Using a positioning algorithm responsive to sensor signals indicating a rotational position of the drive coupling, the RF electrode can be oscillated in the range from 20 Hz to 2000 Hz. Often, oscillation of the RF electrode at a rate ranging from 40 Hz to 400 Hz.

In an eighth aspect, the present invention comprises a method for providing information from a surgical probe to a controller. A hub of the probe is attached to a handpiece connected to the controller. The hub carries indicia, and a first set of data obtained from reading the first set of indicia on the hub may be read using a first sensor on the handpiece, where the first set of data can then be sent to the controller. A second set of indicia on the hub is also read using a second sensor on the handpiece, and a second set of data obtained from the second reading may also be sent to the controller. The first set of data includes at least one of probe identification information and probe orientation information, and the second set of data includes at least probe operational information.

In specific embodiments, the first and/or second set of indicia may comprise magnets, as taught in any of previously described embodiments. In alternative embodiments, however, the first and/or second sets of indicia may comprise optical encoding or any other type of data encoding that can be read using sensors in the handpiece. For example, the first set of indicia may comprise optical encoding including a scannable code on a stationary component of the hub, such as a housing. The first set of indicia incorporates said at least one of probe identification information and probe orientation information and can be read when the code is static relative to the handpiece, typically using a stationary optical scanner, such as a bar or 3D code reader. In other examples, the second set of indicia may comprise optical encoding configured to be read by a scannable code reader, e.g., markings on a rotatable component of the hub, wherein at least the probe operational information is configured to read from the markings as the rotatable component dynamically rotates. For example, the markings may be read by an optical counter that can determine a rotation speed, such as revolutions per minute (RPM).

BRIEF DESCRIPTION OF THE DRAWINGS

Various embodiments of the present invention will now be discussed with reference to the appended drawings. It should be appreciated that the drawings depict only typical embodiments of the invention and are therefore not to be considered limiting in scope.

FIG. 25A is a perspective view of the probe of FIGS. 22 and 23 showing the hub and shaft of the probe.

FIG. 25B is a longitudinal sectional view of the probe of FIG. 25A.

FIG. 28A is an enlarged perspective view of the inner sleeve assembly and burr of the probe of FIG. 27.

FIG. 28B is a perspective view of the outer sleeve of the probe of FIG. 27.

DETAILED DESCRIPTION OF THE INVENTION

The present invention relates to bone cutting and tissue removal devices and related methods of use. Several variations of the invention will now be described to provide an overall understanding of the principles of the form, function and methods of use of the devices disclosed herein. In general, the present disclosure provides for variations of arthroscopic tools adapted for cutting bone, soft tissue, meniscal tissue, and for RF ablation and coagulation. The arthroscopic tools are typically disposable and are configured for detachable coupling to a non-disposable handpiece that carries a motor drive component. This description of the general principles of this invention is not meant to limit the inventive concepts in the appended claims.

Figure 1:
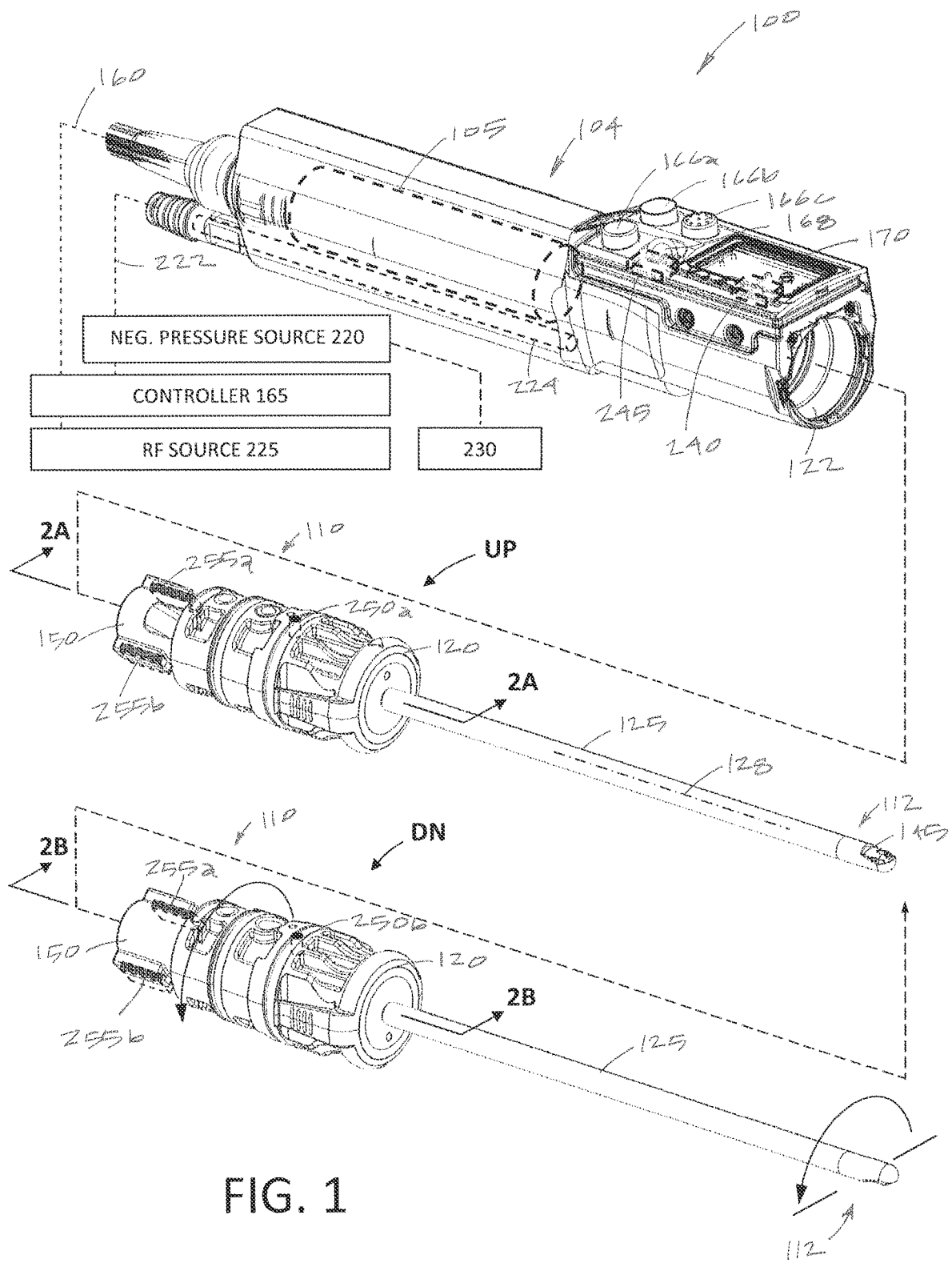
FIG. 1 is a perspective view of an arthroscopic cutting system that includes reusable handpiece with a motor drive and a detachable single-use cutting probe, wherein the cutting probe is shown in two orientations as it may be coupled to the handpiece with the probe and working end in upward orientation or a downward orientation relative to the handpiece, and wherein the handpiece includes an LCD screen for displaying operating parameters of system during use together with control actuators on the handpiece.

In one variation shown in FIG. 1, the arthroscopic system 100 of the present invention provides a handpiece 104 with motor drive 105 and a disposable shaver assembly or probe 110 with a proximal hub 120 that can be received by receiver or bore 122 in the handpiece 104. In one aspect, the probe 110 has a working end 112 that carries a high-speed rotating cutter that is configured for use in many arthroscopic surgical applications, including but not limited to treating bone in shoulders, knees, hips, wrists, ankles and the spine.

Figure 2A:
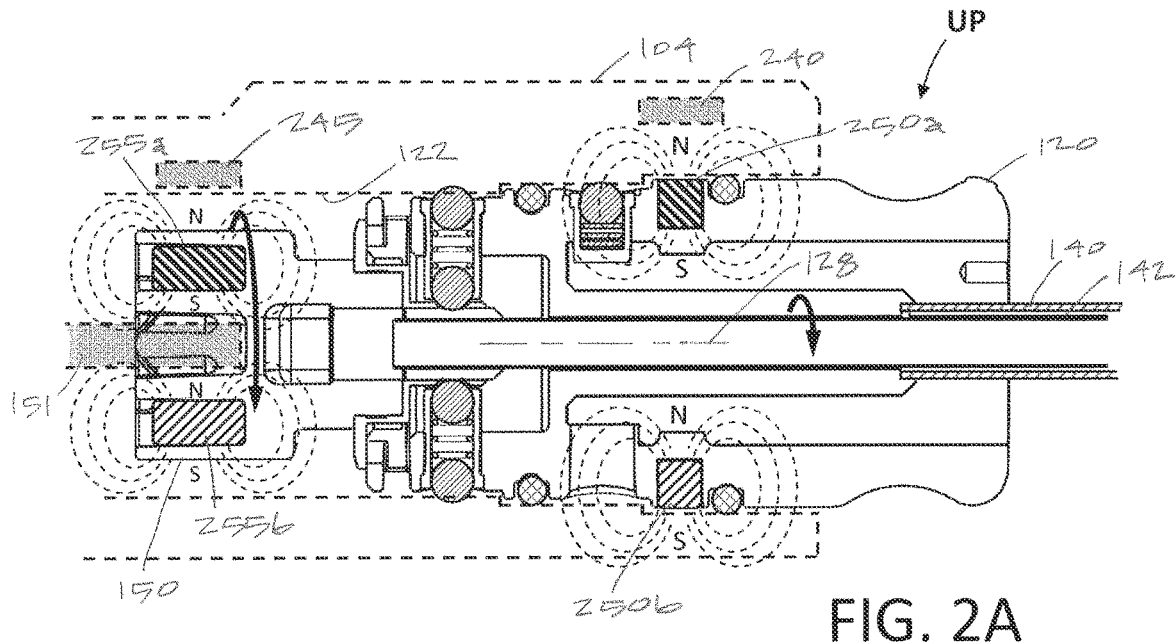
FIG. 2A is an enlarged longitudinal sectional view of the hub of the probe of FIG. 1 taken along line 2A-2A of FIG. 1 with the hub and probe in an upward orientation relative to the handpiece, further showing Hall effect sensors carried by the handpiece and a plurality of magnets carried by the probe hub for device identification, for probe orientation and determining the position of motor driven components of the probe relative to the handpiece.
Figure 3A:
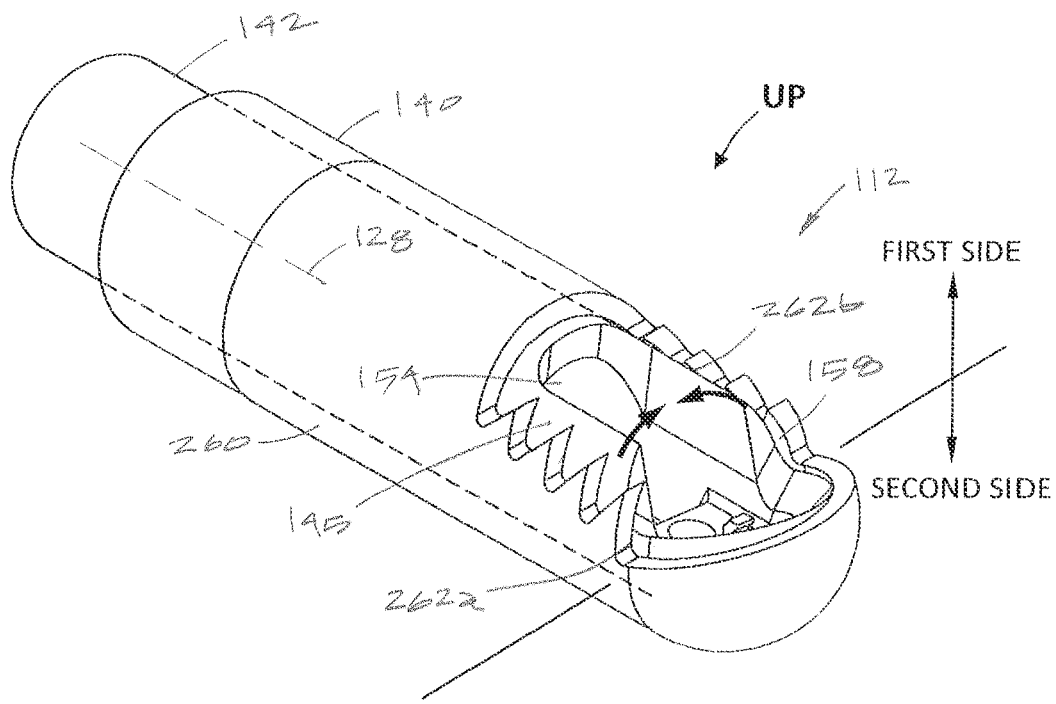
FIG. 3A is an enlarged perspective view of the working end of the probe of FIG. 1 in an upward orientation with the rotatable cutting member in a first position relative to the outer sleeve wherein the window in the cutting member is aligned with the window of the outer sleeve.
Figure 3B:
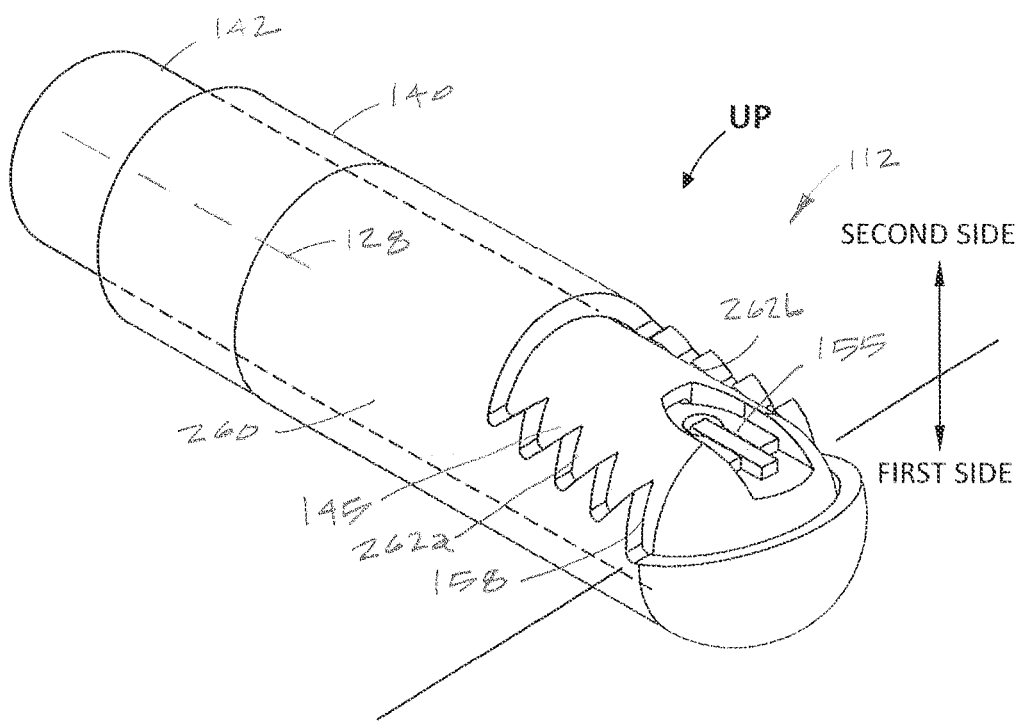
FIG. 3B is a perspective view of the working end of FIG. 1 in an upward orientation with the rotatable cutting member in a second position relative to the outer sleeve wherein the electrode carried by the cutting member is aligned with a centerline of the window of the outer sleeve.

In FIGS. 1, 2A and 3A, it can be seen that probe 110 has a shaft 125 extending along longitudinal axis 128 that comprises an outer sleeve 140 and an inner sleeve 142 rotatably disposed therein with the inner sleeve 142 carrying a distal ceramic cutting member 145 (FIG. 3A). The shaft 125 extends from the proximal hub 120 wherein the outer sleeve 140 is coupled in a fixed manner to the hub 120 which can be an injection molded plastic, for example, with the outer sleeve 140 insert molded therein. The inner sleeve 142 is coupled drive coupling 150 that is configured for coupling to the rotating motor shaft 151 of motor drive unit 105. More in particular, the rotatable cutting member 145 that is fabricated of a ceramic material with sharp cutting edges on opposing sides 152a and 152b of window 154 therein for cutting soft tissue. The motor drive 105 is operatively coupled to the ceramic cutter to rotate the cutting member at speeds ranging from 1,000 rpm to 20,000 rpm. In FIG. 3B, it can be seen that cutting member 145 also carries an RF electrode 155 in a surface opposing the window 154. The cutting member 145 rotates and shears tissue in the toothed opening or window 158 in the outer sleeve 140 (FIG. 3A). A probe of the type shown in FIG. 1 is described in more detail in co-pending and commonly owned patent application Ser. No. 15/421,264 filed Jan. 31, 2017 titled ARTHROSCOPIC DEVICES AND METHODS which is incorporated herein in its entirety by this reference.

As can be seen in FIG. 1, the probe 110 is shown in two orientations for detachable coupling to the handpiece 104. More particularly, the hub 120 can be coupled to the handpiece 104 in an upward orientation indicated at UP and a downward orientation indicated at DN where the orientations are 180° opposed from one another. It can be understood that the upward and downward orientations are necessary to orient the working end 112 either upward or downward relative to the handpiece 104 to allow the physician to interface the cutting member 145 with targeted tissue in all directions without having to manipulate the handpiece in 360° to access tissue.

In FIG. 1, it can be seen that the handle 104 is operatively coupled by electrical cable 160 to a controller 165 which controls the motor drive unit 105 Actuator buttons 166a, 166b or 166c on the handle 104 can be used to select operating modes, such as various rotational modes for the ceramic cutting member 145. In one variation, a joystick 168 can be moved forward and backward to adjust the rotational speed of the ceramic cutting member 145. The rotational speed of the cutter can continuously adjustable, or can be adjusted in increments up to 20,000 rpm. An LCD screen 170 is provided in the handpiece for displaying operating parameters, such as cutting member RPM, mode of operation, etc.

Figure 4:
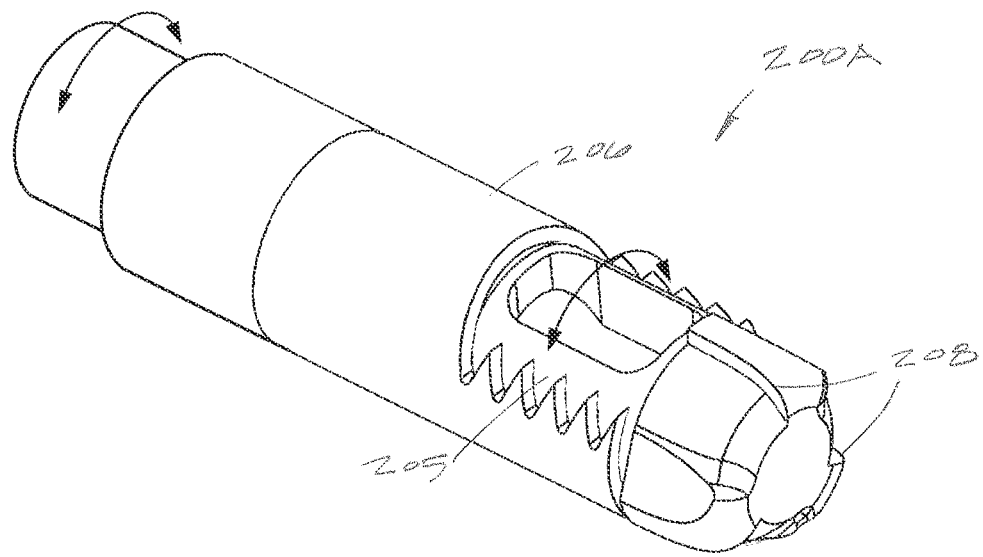
FIG. 4 is a perspective view of a working end of a variation of a probe that may be detachably coupled to the handpiece of FIG. 1, wherein the working end includes a bone burr extending distally from the outer sleeve.
Figure 5:
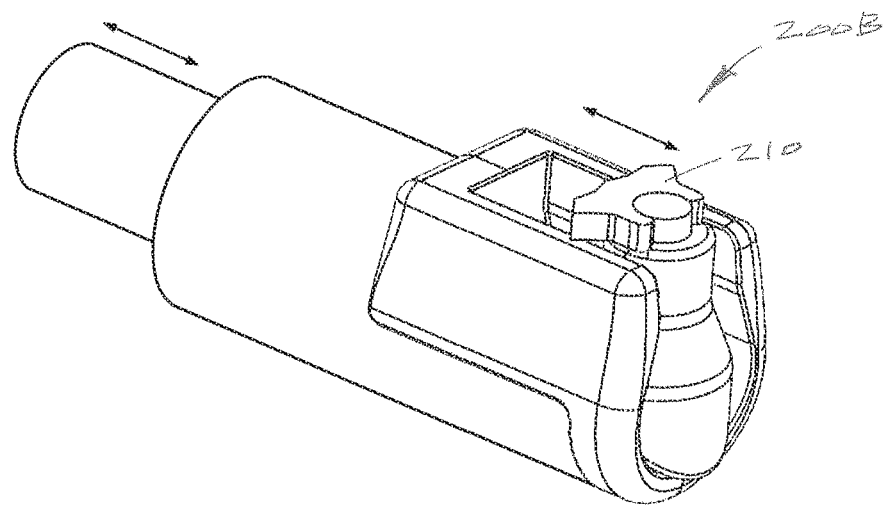
FIG. 5 is a perspective view of a working end of a variation of a probe that may be detachably coupled to the handpiece of FIG. 1, wherein the working end has a reciprocating electrode.
Figure 6:
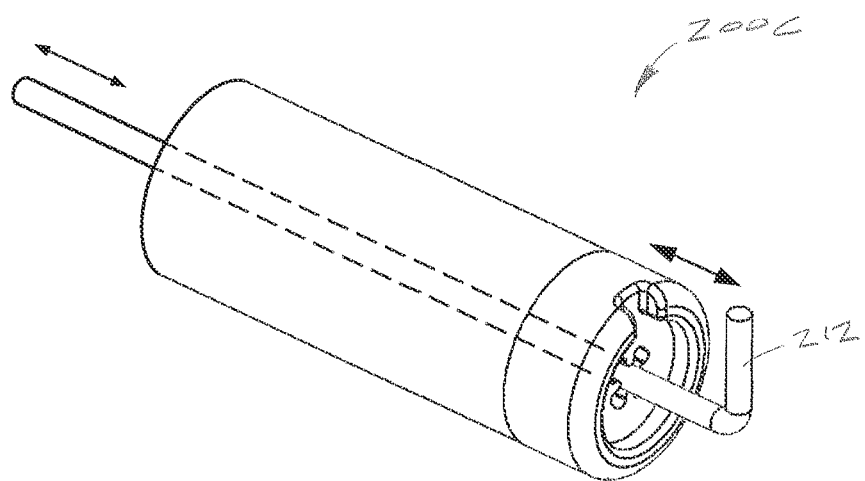
FIG. 6 is a perspective view of a working end of another variation of a probe that may be detachably coupled to the handpiece of FIG. 1, wherein the working end has a hook electrode that has extended and non-extended positions.
Figure 7:
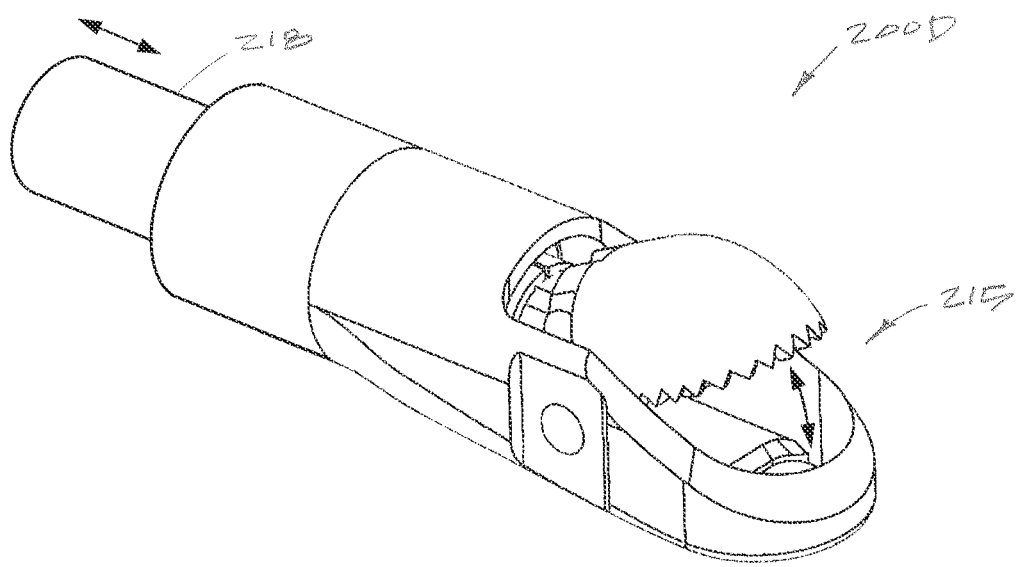
FIG. 7 is a perspective view of a working end of yet another variation of a probe that may be detachably coupled to the handpiece of FIG. 1, wherein the working end has an openable-closeable jaw structure for cutting tissue.

It can be understood from FIG. 1 that the system 100 and handpiece 104 is adapted for use with various disposable probes which can be designed for various different functions and procedures For example, FIG. 4 illustrates a different variation of a probe working end 200A that is similar to working end 112 of probe 110 of FIGS. 3A-3B, except the ceramic cutting member 205 extends distally from the outer sleeve 206 and the cutting member has burr edges 208 for cutting bone. The probe of FIG. 4 is described in more detail in co-pending and commonly owned patent application Ser. No. 15/271,184 filed Sep. 20, 2016 titled ARTHROSCOPIC DEVICES AND METHODS. FIG. 5 illustrates a different variation of a probe working end 200B with a reciprocating electrode 210 in a type of probe described in more detail in co-pending and commonly owned patent application Ser. No. 15/410,723 filed Jan. 19, 2017 titled ARTHROSCOPIC DEVICES AND METHODS. In another example, FIG. 6 illustrates another variation of a probe working end 200C that has an extendable-retractable hook electrode 212 in a probe type described in more detail in co-pending and commonly owned patent application Ser. No. 15/454,342 filed Mar. 9, 2017 titled ARTHROSCOPIC DEVICES AND METHODS. In yet another example, FIG. 7 illustrates a variation of a working end 200D in a probe type having an openable-closable jaw structure 215 actuated by reciprocating member 218 for trimming meniscal tissue or other tissue as described in more detail in co-pending and commonly owned patent application Ser. No. 15/483,940 filed Apr. 10, 2017 titled ARTHROSCOPIC DEVICES AND METHODS. All of the probes of FIGS. 4-7 can have a hub similar to hub 120 of probe 110 of FIG. 1 for coupling to the same handpiece 104 of FIG. 1, with some of the probes (see FIGS. 5-7) having a hub mechanism for converting rotational motion to linear motion. All of the patent applications just identified in this paragraph are incorporated herein by this reference.

FIG. 1 further shows that the system 100 also includes a negative pressure source 220 coupled to aspiration tubing 222 which communicates with a flow channel 224 in handpiece 104 and can cooperate with any of the probes 110, 200A, 200B or 200C of FIGS. 1-3B, 4, 5 and 6. In FIG. 1 it also can be seen that the system 100 includes an RF source 225 which can be connected to an electrode arrangement in any of the probes 110, 200A, 200B or 200C of FIGS. 1-3B, 4, 5 and 6. The controller 165 and microprocessor therein together with control algorithms are provided to operate and control all functionality, which includes controlling the motor drive 105 to move a motor-driven component of any probe working end 110, 200A, 200B or 200C, as well as for controlling the RF source 225 and the negative pressure source 220 which can aspirate fluid and tissue debris to collection reservoir 230.

As can be understood from the above description of the system 100 and handpiece 104, the controller 165 and controller algorithms need to be configured to perform and automate many tasks to provide for system functionality. In a first aspect, controller algorithms are needed for device identification so that when any of the different probes types 110, 200A, 200B, 200C or 200D of FIGS. 1 and 4-7 are coupled to handpiece 104, the controller 165 will recognize the probe type and then select algorithms for operating the motor drive 105, RF source 225 and negative pressure source 220 as is needed for the particular probe. In a second aspect, the controller is configured with algorithms that identify whether the probe is coupled to the handpiece 104 in an upward or downward orientation relative to the handpiece, wherein each orientation requires a different subset of the operating algorithms. In another aspect, the controller has separate control algorithms for each probe type wherein some probes have a rotatable cutter while others have a reciprocating electrode or jaw structure. In another aspect, most if not all the probes 110, 200A, 200B, 200C and 200D (FIGS. 1, 4-7) require a default "stop" position in which the motor-driven component is stopped in a particular orientation within the working end. For example, a rotatable cutter 145 with an electrode 155 needs to have the electrode centered within an outer sleeve window 158 in a default position such as depicted in FIG. 3B. Some of these systems, algorithms and methods of use are described next.

Figure 2B:
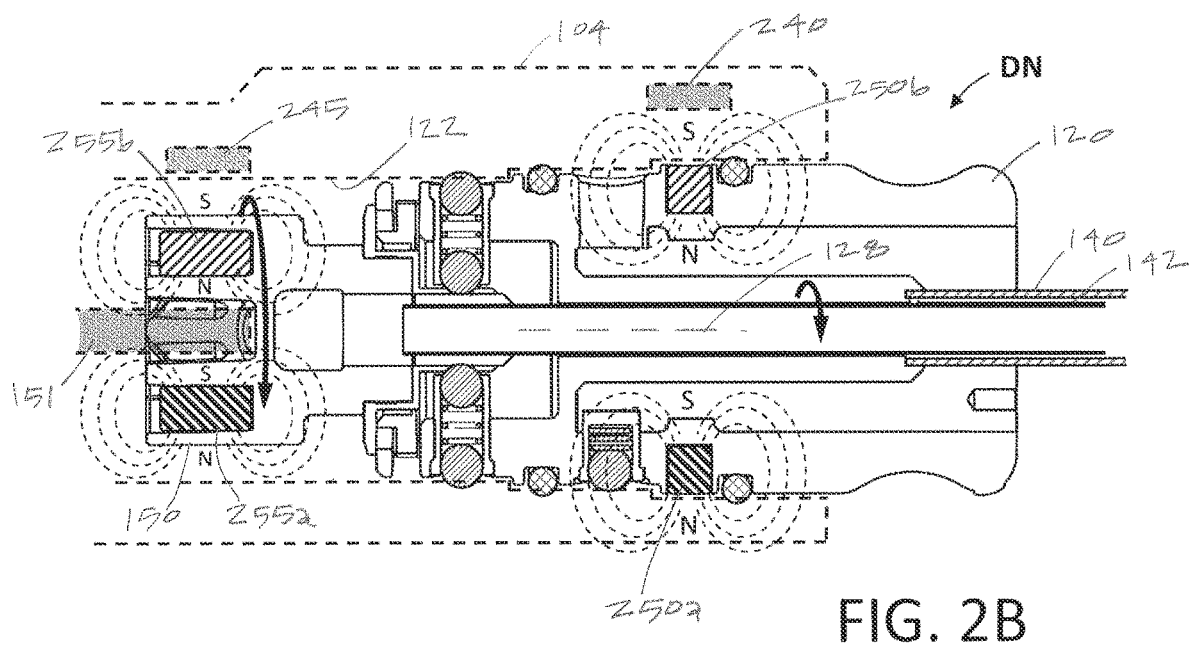
FIG. 2B is a sectional view of the hub of FIG. 1 taken along line 2B-2B of FIG. 1 with the hub and probe in a downward orientation relative to the handpiece showing the Hall effect sensor and magnets having a different orientation compared to that of FIG. 2A.

Referring to FIGS. 1 and 2A-2B, it can be seen that handpiece 104 carries a first Hall effect sensor 240 in a distal region of the handpiece 104 adjacent the receiving passageway 122 that receives the hub 120 of probe 110. FIG. 2A corresponds to the probe 110 and working end 112 in FIG. 1 being in the upward orientation indicated at UP. FIG. 2B corresponds to probe 110 and working end 112 in FIG. 1 being in the downward orientation indicated at DN. The handpiece 104 carries a second Hall effect sensor 245 adjacent the rotatable drive coupling 150 of the probe 110. The probe 110 carries a plurality of magnets as will be described below that interact with the Hall effect sensors 240, 245 to provide multiple control functions in cooperation with controller algorithms, including (i) identification of the type of probe coupled to the handpiece, (ii) the upward or downward orientation of the probe hub 120 relative to the handpiece 104, and (iii) the rotational position and speed of rotating drive collar 150 from which a position of either rotating or reciprocating motor-driven components can be determined.

The sectional views of FIGS. 2A-2B show that hub 120 of probe 110 carries first and second magnets 250a and 250b in a surface portion thereof. The Hall sensor 240 in handpiece 104 is in axial alignment with either magnet 250a or 250b when the probe hub 120 is coupled to handpiece 104 in an upward orientation (FIGS. 1 and 2A) or a downward orientation (FIGS. 1 and 2B). In one aspect as outlined above, the combination of the magnets 250a and 250b and the Hall sensor 240 can be used to identify the probe type. For example, a product portfolio may have from 2 to 10 or more types of probes, such as depicted in FIGS. 1 and 4-7, and each such probe type can carry magnets 250a, 250b having a specific, different magnetic field strength. Then, the Hall sensor 240 and controller algorithms can be adapted to read the magnetic field strength of the particular magnet(s) in the probe which can be compared to a library of field strengths that correspond to particular probe types. Then, a Hall identification signal can be generated or otherwise provided to the controller 165 to select the controller algorithms for operating the identified probe, which can include parameters for operating the motor drive 105, negative pressure source 220 and/or RF source 225 as may be required for the probe type. As can be seen in FIGS. 1, 2A and 2B, the probe hub 120 can be coupled to handpiece 104 in upward and downward orientations, in which the North (N) and South (S) poles of the magnets 250a, 250b are reversed relative to the probe axis 128. Therefore, the Hall sensor 240 and associated algorithms look for magnetic field strength regardless of polarity to identify the probe type.

Referring now to FIGS. 1, 2A-2B and 3A-3B, the first and second magnets 250a and 250b with their different orientations of North (N) and South (S) poles relative to central longitudinal axis 128 of hub 120 are also used to identify the upward orientation UP or the downward orientation DN of hub 120 and working end 112. In use, as described above, the physician may couple the probe 110 to the handpiece receiving passageway 122 with the working end 112 facing upward or downward based on his or her preference and the targeted tissue. It can be understood that controller algorithms adapted to stop rotation of the cutting member 145 in the window 158 of the outer sleeve 104 of working end 112 need to "learn" whether the working end is facing upward or downward, because the orientation or the rotating cutting member 145 relative to the handpiece and Hall sensor 240 would vary by 180°. The Hall sensor 240 together with a controller algorithm can determine the orientation UP or the downward orientation DN by sensing whether the North (N) or South (S) pole of either magnet 250a or 250b is facing upwardly and is proximate the Hall sensor 240.

In another aspect of the invention, in probe 110 (FIG. 1) and other probes, the motor-driven component of a working end, such as rotating cutter 145 of working end 112 of FIGS. 1 and 3A-3B needs to stopped in a selected rotational position relative to a cut-out opening or window 158 in the outer sleeve 140. Other probe types may have a reciprocating member or a jaw structure as described above, which also needs a controller algorithm to stop movement of a moving component in a selected position, such as the axial-moving electrodes of FIGS. 5-6 and the jaw structure of FIG. 7. In all probes, the motor drive 105 couples to the rotating drive coupling 150, thus sensing the rotational position of the drive coupling 150 can be used to determine the orientation of the motor-driven component in the working end. More in particular, referring to FIGS. 1 and 2A-2B, the drive coupling 150 carries third and fourth magnets 255a or 255b with the North (N) and South (S) poles of magnets 255a or 255b being reversed relative to the probe axis 128. Thus, Hall sensor 245 can sense when each magnet rotates passes the Hall sensor and thereby determine the exact rotational position of the drive coupling 150 twice on each rotation thereof (once for each magnet 255a, 255b). Thereafter, a controller tachometer algorithm using a clock can determine and optionally display the RPM of the drive coupling 150 and, for example, the cutting member 145 of FIG. 3A.

In another aspect of the invention, the Hall sensor 245 and magnets 255a and 255b (FIGS. 1 and 2A) are used in a set of controller algorithms to stop the rotation of a motor-driven component of a working end, for example, cutting member 145 of FIGS. 1 and 3A-3B in a preselected rotational position. In FIG. 3A, it can be seen that the inner sleeve 142 and a "first side" of cutting member 145 and window 154 therein is stopped and positioned in the center of window 158 of outer sleeve 140. The stationary position of cutting member 145 and window 154 in FIG. 3A may be used for irrigation or flushing of a working space to allow for maximum fluid outflow through the probe.

FIG. 3B depicts inner sleeve 142 and a "second side" of cutting member 145 positioned about the centerline of window 158 in the outer sleeve 140. The stationary or stopped position of cutting member 145 in FIG. 3B is needed for using the RF electrode 155 to ablate or coagulate tissue. It is important that the electrode 155 is maintained along the centerline of the outer sleeve window 158 since the outer sleeve 140 typically comprises return electrode 260. The position of electrode 155 in FIG. 3B is termed herein a "centerline default position". If the cutting member 145 and electrode 155 were rotated so as to be close to an edge 262a or 262b of window 158 in outer sleeve 140, RF current could arc between the electrodes 155 and 260 and potentially cause a short circuit disabling the probe. Therefore, a robust and reliable stop mechanism is required which is described next.

As can be understood from FIGS. 1 and 2A-2B, the controller 165 can always determine in real time the rotational position of drive coupling 150 and therefore the angular or rotational position of the ceramic cutting member 145 and electrode 155 can be determined. A controller algorithm can further calculate the rotational angle of the electrode 155 away from the centerline default position as drive coupling 150 rotates the electrode 155 away from the centerline default position. Each magnet has a specified, known strength and the algorithm can use a look-up table with that lists fields strengths corresponding to degrees of rotation away from the default position. Thus, if the Hall signal responsive to the rotated position of magnet 255a or 255b drops a specified amount from a known peak value in the centerline default position, it means the electrode 155 has moved away from the center of the window 158. In one variation, if the electrode 155 moves a selected rotational angle away from the centerline position during RF energy delivery to the electrode, the algorithm turns off RF current instantly and alerts the physician by an aural and/or visual signal, such as an alert on the LCD screen 170 on handpiece 104 and/or on a screen on a controller console (not shown). The termination of RF current delivery thus prevents the potential of an electrical arc between electrode 155 and the outer sleeve electrode 260.

It can be understood that during use, when the electrode 155 is in the position shown in FIG. 3B, the physician may be moving the energized electrode over tissue to ablate or coagulate tissue. During such use, the cutting member 145 and electrode 155 can engage or catch on tissue which inadvertently rotate the electrode 155 out of the default centerline position. Therefore, the system provides a controller algorithm, herein called an "active electrode monitoring" algorithm, wherein the controller continuously monitors position signals generated by Hall sensor 245 during RF energy delivery in both an ablation mode and a coagulation mode to determine if the electrode 155 and inner sleeve 142 have been bumped off the centerline position. In a variation, the controller algorithms can be configured to then re-activate the motor drive 105 to move the inner sleeve 142 and electrode 155 back to the default centerline position sleeve if electrode 155 had been bumped off the centerline position. In another variation, the controller algorithms can be configured to again automatically deliver RF current to RF electrode 155 when it is moved back to the to the default centerline position. Alternatively, the controller 165 can require the physician to manually re-start the delivery of RF current to the RF electrode 155 when it is moved back to the to the centerline position. In an aspect of the invention, the drive coupling 150 and thus magnets 255a and 255b are attached to inner sleeve 142 and cutting member 145 in a pre-determined angular relationship relative to longitudinal axis 128 so that the Hall sensor generates signals responsive to magnets 255a, 255b is the same for all probes within a probe type to thus allow the controller algorithm to function properly.

Figure 8:
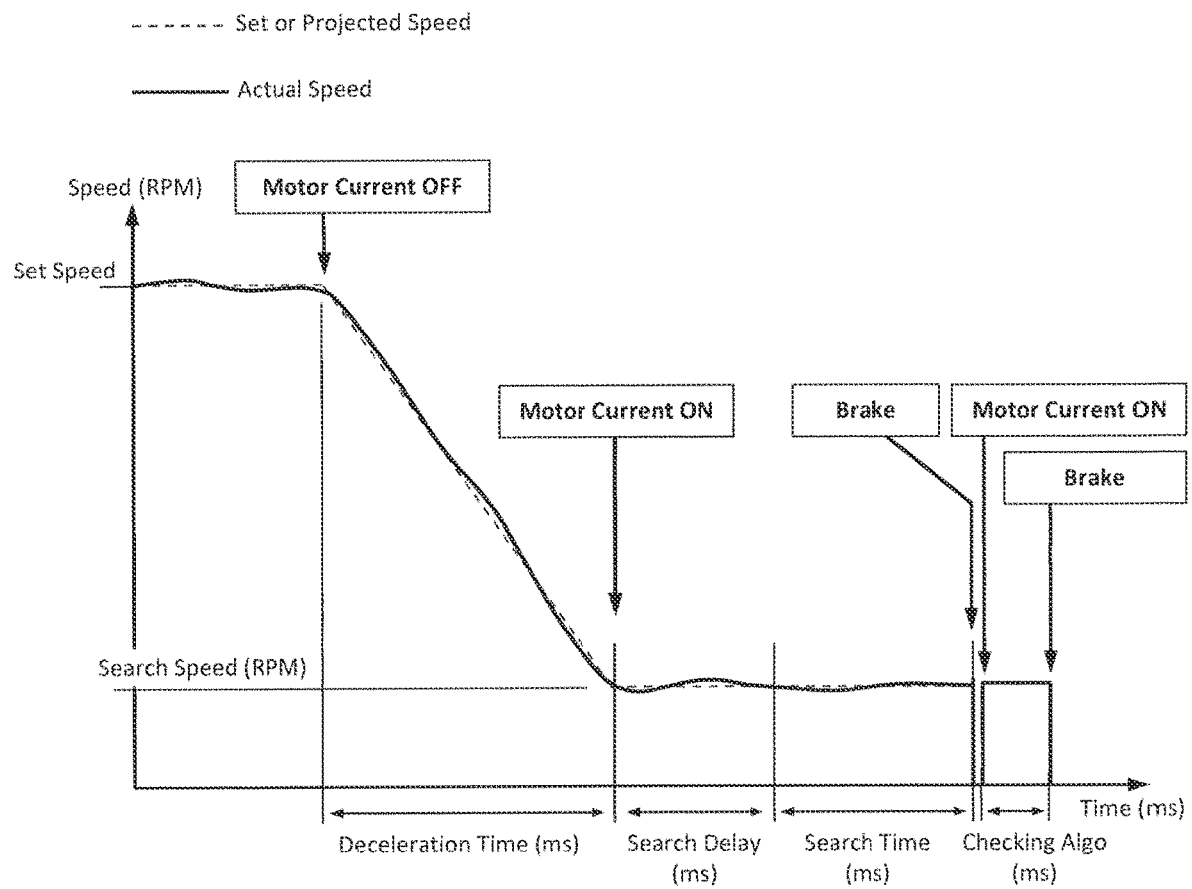
FIG. 8 is a chart relating to set speeds for a probe with a rotating cutting member as in FIGS. 1 and 3A that schematically shows the method used by a controller algorithm for stopping rotation of the cutting member in a selected default position.

Now turning to the stop mechanism or algorithms for stopping movement of a motor-driven component of working end 112, FIG. 8 schematically illustrates the algorithm and steps of the stop mechanism. In one variation, referring to FIG. 8, the stop mechanism corresponding to the invention uses (i) a dynamic braking method and algorithm to stop the rotation of the inner sleeve 142 and cutting member 145 (FIGS. 1, 3A-3B) in an initial position, and thereafter (ii) a secondary checking algorithm is used to check the initial stop position that was attained with the dynamic braking algorithm, and if necessary, the stop algorithm can re-activate the motor drive 105 to slightly reverse (or move forward) the rotation of drive coupling 150 and inner sleeve 142 as needed to position the cutting member 145 and electrode 155 within at the centerline position or within 0° to 5° of the targeted centerline default position. Dynamic braking is described further below. FIG. 8 schematically illustrates various aspects of controller algorithms for controlling the rotational speed of the cutting member and for stopping the cutting member 145 in the default centerline position.

In FIG. 8, it can be understood that the controller 165 is operating the probe 110 of FIGS. 1 and 3A-3B at a "set speed" which may be a PID controlled, continuous rotation mode in one direction or may be an oscillating mode where the motor drive 105 rotates the cutting member 145 in one direction and then reverses rotation as is known in the art. At higher rotational speeds such as 1,000 RPM to 20,000 RPM, it is not practical or feasible to acquire a signal from Hall sensor 245 that indicates the position of a magnet 255a or 255b in the drive coupling 150 to apply a stop algorithm. In FIG. 8, when the physician stop cutting with probe 110 by releasing actuation of an actuator button or foot pedal, current to the motor drive 105 is turned off. Thereafter, the controller algorithm uses the Hall sensor 245 to monitor deceleration of rotation of the drive coupling 150 and inner sleeve 142 until a slower RPM is reached. The deceleration period may be from 10 ms to 1 sec and typically is about 100 ms. When a suitable slower RPM is reached which is called a "search speed" herein (see FIG. 8), the controller 165 re-activates the motor drive 105 to rotate the drive coupling at a low speed ranging from 10 RPM to 1,000 RPM and in one variation is between 50 RPM and 250 RPM. An initial "search delay" period ranging from 50 ms to 500 ms is provided to allow the PLD controller to stabilize the RPM at the selected search speed. Thereafter, the controller algorithm monitors the Hall position signal of magnet strength and when the magnet parameter reaches a predetermined threshold, for example, when the rotational position of drive coupling 150 and electrode 155 correspond to the centerline default position of FIG. 3B, the control algorithm then applies dynamic braking to instantly stop rotation of the motor drive shaft 151, drive coupling 150 and the motor-driven component of the probe. FIG. 8 further illustrates that the controller can check the magnet/drive coupling 150 position after the braking and stopping steps. If the Hall position signal indicates that the motor-driven component is out of the targeted default position, the motor drive 105 can be re-activated to move the motor-driven component and thereafter the brake can be applied again as described above.

Dynamic braking as shown schematically in FIG. 8 may typically stop the rotation of the drive coupling 150 with a variance of up to about 0°-15° of the targeted stop position, but this can vary even further when different types of tissue are being cut and impeding rotation of the cutting member 145, and also depending on whether the physician has completely disengaged the cutting member from the tissue interface when the motor drive is de-activated. Therefore, dynamic braking alone may not assure that the default or stop position is within a desired variance.

As background, the concept of dynamic braking is described in the following literature: https://www.ab.com/support/abdrives/documentation/tech-papers/RegenOverview01.pdf and http://literature.rockwellautomation.com/idc/groups/literature/documents/wp/drives-wp004_-en-p.pdf. Basically, a dynamic braking system provides a chopper transistor on the DC bus of the AC PWM drive that feeds a power resistor that transforms the regenerative electrical energy into heat energy. The heat energy is dissipated into the local environment. This process is generally called dynamic braking with the chopper transistor and related control and components called the chopper module and the power resistor called the dynamic brake resistor. The entire assembly of chopper module with dynamic brake resistor is sometimes referred to as the dynamic brake module. The dynamic brake resistor allows any magnetic energy stored in the parasitic inductance of that circuit to be safely dissipated during the turn off of the chopper transistor.

The method is called dynamic braking because the amount of braking torque that can be applied is dynamically changing as the load decelerates. In other words, the braking energy is a function of the kinetic energy in the spinning mass and as it declines, so does the braking capacity. So the faster it is spinning or the more inertia it has, the harder you can apply the brakes to it, but as it slows, you run into the law of diminishing returns and at some point, there is no longer any braking power left.

In another aspect of the invention, a method has been developed to increase the accuracy of the stopping mechanism which is a component of the positioning algorithm described above. It has been found that each magnet in a single-use probe may vary slightly from its specified strength. As described above, the positioning algorithm uses the Hall effect sensor 245 to continuously monitor the field strength of magnets 255a and 255b as the drive coupling 150 rotates and the algorithm determines the rotational position of the magnets and drive coupling based on the field strength, with the field strength rising and falling as a magnet rotates past the Hall sensor. Thus, it is important for the algorithm to have a library of fields strengths that accurately correspond to degrees of rotation away from a peak Hall signal when a magnet is adjacent the sensor 245. For this reason, an initial step of the positioning algorithm includes a "learning" step that allow the controller to learn the actual field strength of the magnets 255a and 255b which may vary from the specified strength. After a new single-use probe 110 (FIG. 1) is coupled to the handpiece 104, and after actuation of the motor drive 105, the positioning algorithm will rotate the drive coupling at least 180° and more often at least 360° while the Hall sensor 245 quantifies the field strength of the particular probe's magnets 255a and 255b. The positioning algorithm then stores the maximum and minimum Hall signals (corresponding to North and South poles) and calibrates the library of field strengths that correspond to various degrees of rotation away from a Hall min-max signal position when a magnet is adjacent the Hall sensor.

In general, a method of use relating to the learning algorithm comprises providing a handpiece with a motor drive, a controller, and a probe with a proximal hub configured for detachable coupling to the handpiece, wherein the motor drive is configured to couple to a rotating drive coupling in the hub and wherein the drive coupling carries first and second magnets with North and South poles positioned differently relative to said axis, and coupling the hub to the handpiece, activating the motor drive to thereby rotate the drive coupling and magnets at least 180°, using a handpiece sensor to sense the strength of each magnet, and using the sensed strength of the magnets for calibration in a positioning algorithm that is responsive to the sensor sensing the varying strength of the magnets in the rotating drive coupling to thereby increase accuracy in calculating the rotational position of the drive coupling 150.

Another aspect of the invention relates to an enhanced method of use using a probe working end with an electrode, such as the working end 112 of FIGS. 1 and 3B. As described above, a positioning algorithm is used to stop rotation of the electrode 155 in the default centerline position of FIG. 3B. An additional "slight oscillation" algorithm is used to activate the motor drive 105 contemporaneous with RF current to the electrode 155, particularly an RF cutting waveform for tissues ablation. The slight oscillation thus provides for a form of oscillating RF ablation. The slight oscillation algorithm rotates the electrode 155 in one direction to a predetermined degree of rotation, which the controller algorithms determine from the Hall position signals. Then, the algorithm reverses direction of the motor drive to rotate in the opposite direction until Hall position signals indicate that the predetermined degree of rotation was achieved in the opposite direction away from the electrode's default centerline position. The predetermined degree of angular motion can be any suitable rotation that is suitable for dimensions of the outer sleeve window, and in one variation is from 1° to 30° in each direction away from the centerline default position. More often, the predetermined degree of angular motion is from 5° to 15° in each direction away from the centerline default. The slight oscillation algorithm can use any suitable PID controlled motor shaft speed, and in one variation the motor shaft speed is from 50 RPM to 5,000 RPM, and more often from 100 RPM to 1,000 RPM. Stated another way, the frequency of oscillation can be from 20 Hz to 2,000 Hz and typically between 40 Hz and 400 Hz.

While the above description of the slight oscillation algorithm is provided with reference to electrode 155 on a rotating cutting member 145 of FIG. 3B, it should be appreciated that a reciprocating electrode 212 as shown in the working end 200C of FIG. 6 end could also be actuated with slight oscillation. In other words, the hook shape electrode 212 of FIG. 6 could be provided with a frequency of oscillation ranging from 20 Hz to 2,000 Hz and typically between 40 Hz and 400 Hz.

Figure 9A:
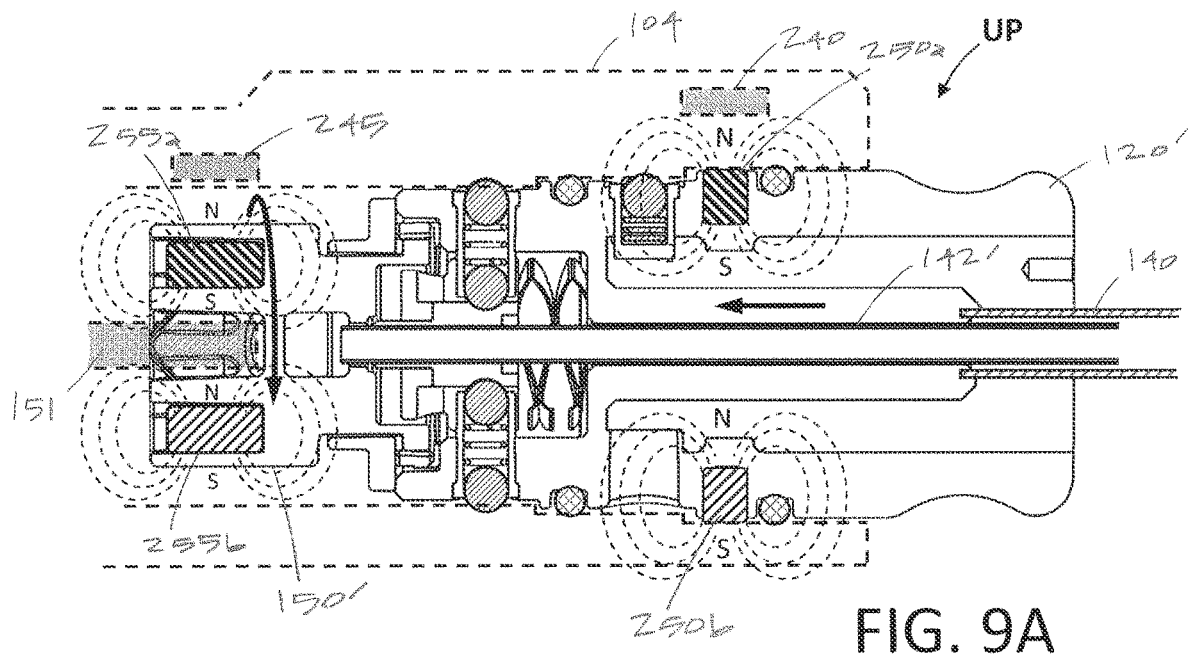
FIG. 9A is a longitudinal sectional view of a probe hub that is similar to that of FIG. 2A, except the hub of FIG. 9A has an internal cam mechanism for converting rotational motion to linear motion to axially reciprocate an electrode as in the working end of FIG. 5, wherein FIG. 9A illustrated the magnets in the hub and drive coupling are the same as in FIG. 2A and the hub is in an upward facing position relative to the handpiece.
Figure 9B:
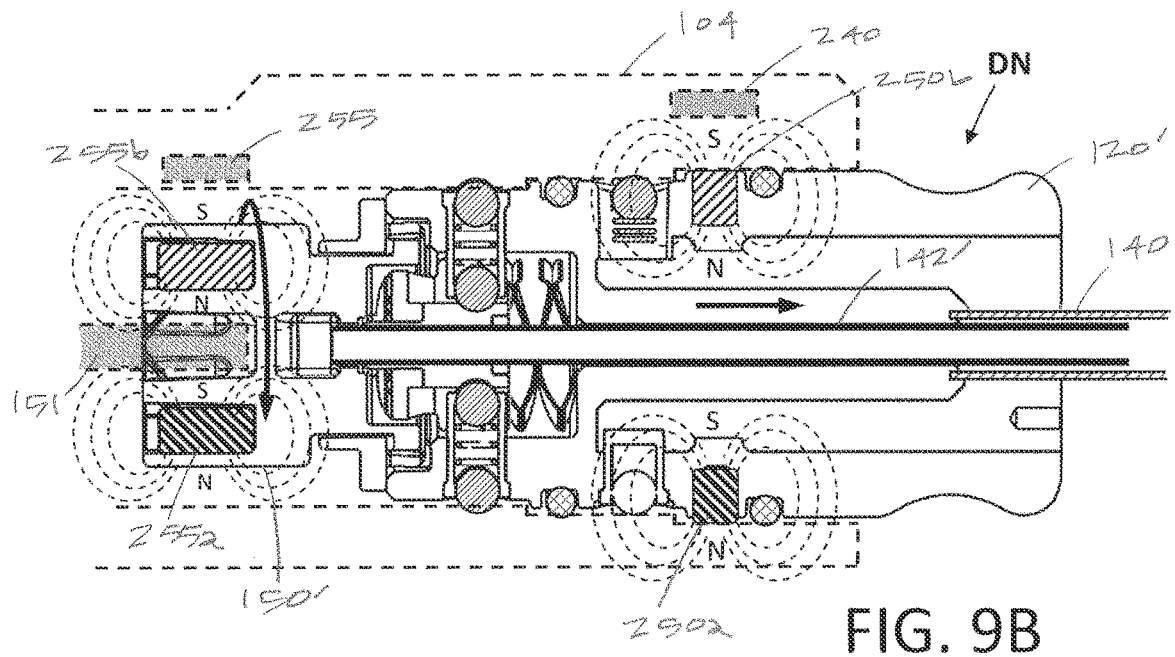
FIG. 9B is a sectional view of the hub of FIG. 9A rotated 180° in a downward facing position relative to the handpiece.

FIGS. 9A-9B are longitudinal sectional views of a probe hub 120' that corresponds to the working end 200B of FIG. 5 which has a reciprocating electrode 210. In FIGS. 9A-9B, the handpiece 104 and Hall affect sensors 240 and 245 are of course the same as described above as there is no change in the handpiece 104 for different types of probes. The probe hub 120' of FIGS. 9A-9B is very similar to the hub 120 of FIGS. 2A-2B with the first and second identification/orientation magnets 250a and 250b being the same. The third and fourth rotation al position magnets 255a and 255b also are the same and are carried by drive coupling 150'. The probe hub 120' of FIGS. 9A-9B only differs in that the drive coupling 150 rotates with a cam mechanism operatively coupled to inner sleeve 142' to convert rotational motion to linear motion to reciprocate the electrode 210 in working end 200B of FIG. 5. A similar hub for converting rotational motion to linear motion is provided for the working ends 200C and 200D of FIGS. 6 and 7, respectively, which each have a reciprocating component (212, 218) in its working end.

Figure 10:
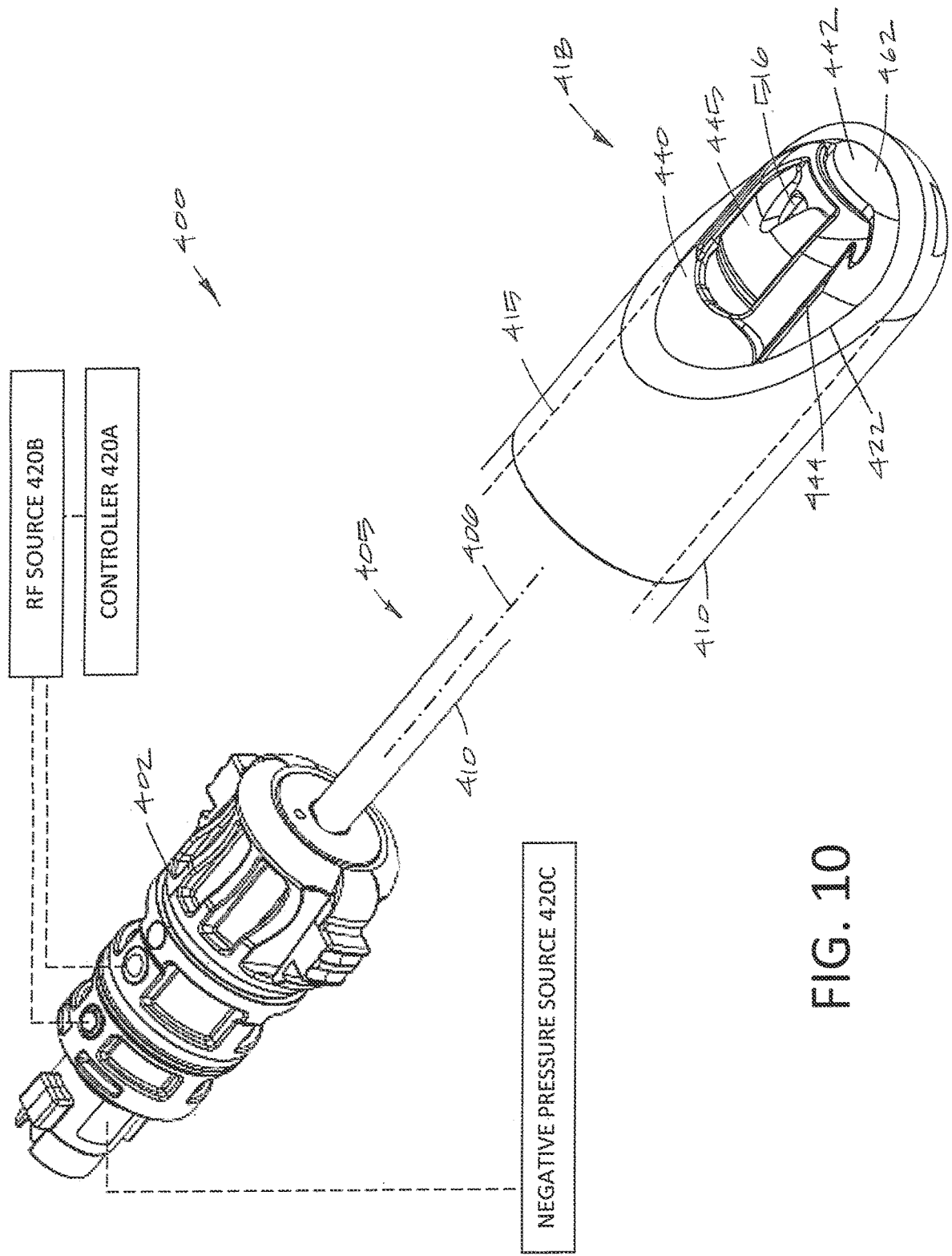
FIG. 10 is a perspective view of another variation of a probe that shows a motor-driven, rotating inner cutting sleeve that includes a longitudinal dielectric member coupled to a longitudinal conductive metal portion, wherein the dielectric member carries an active electrode and the longitudinal conductive metal portion comprises a return electrode.
Figure 11:
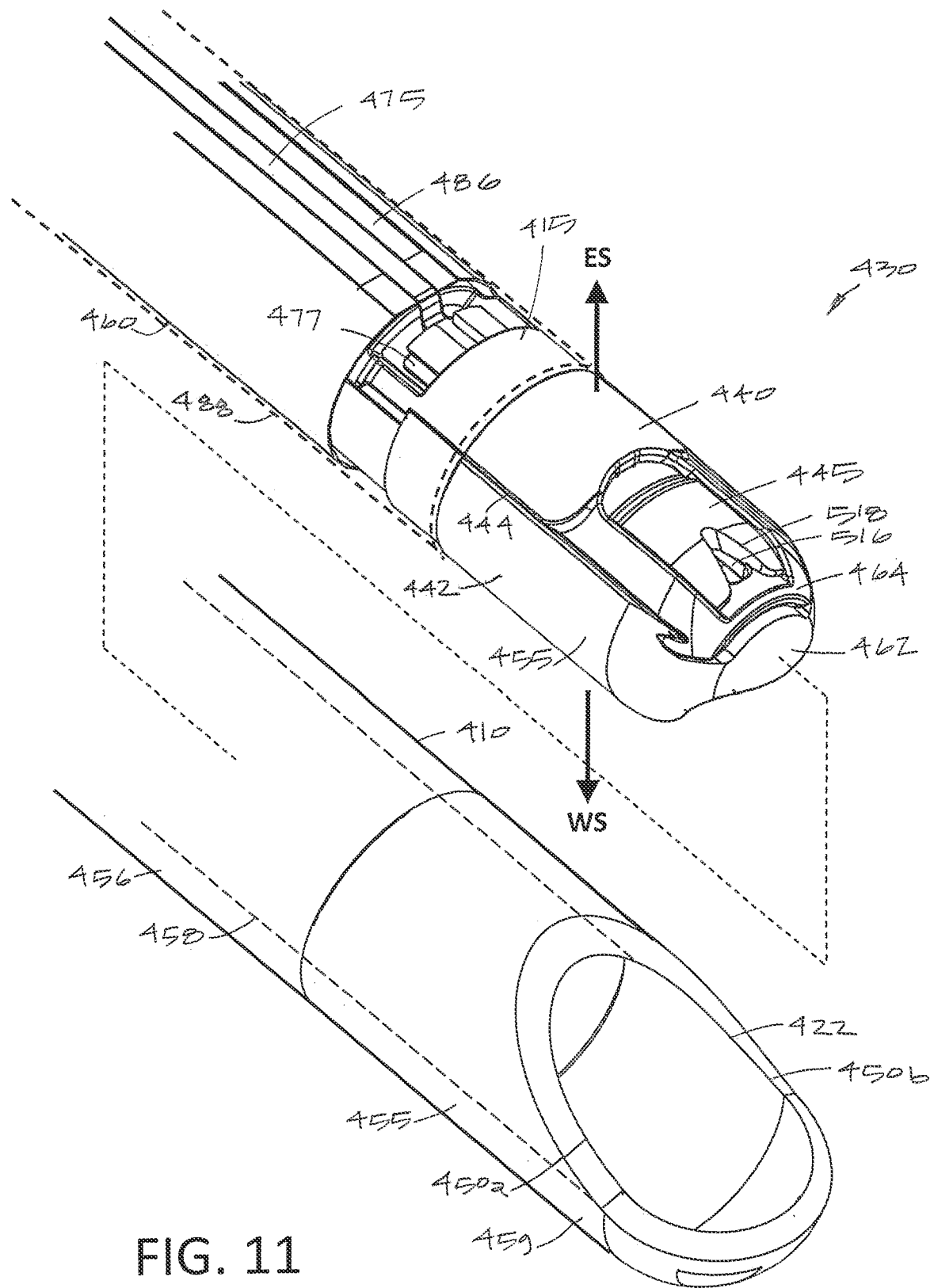
FIG. 11 is an enlarged perspective view of the working end of FIG. 10 with the inner sleeve separated from the outer sleeve.
Figure 12:
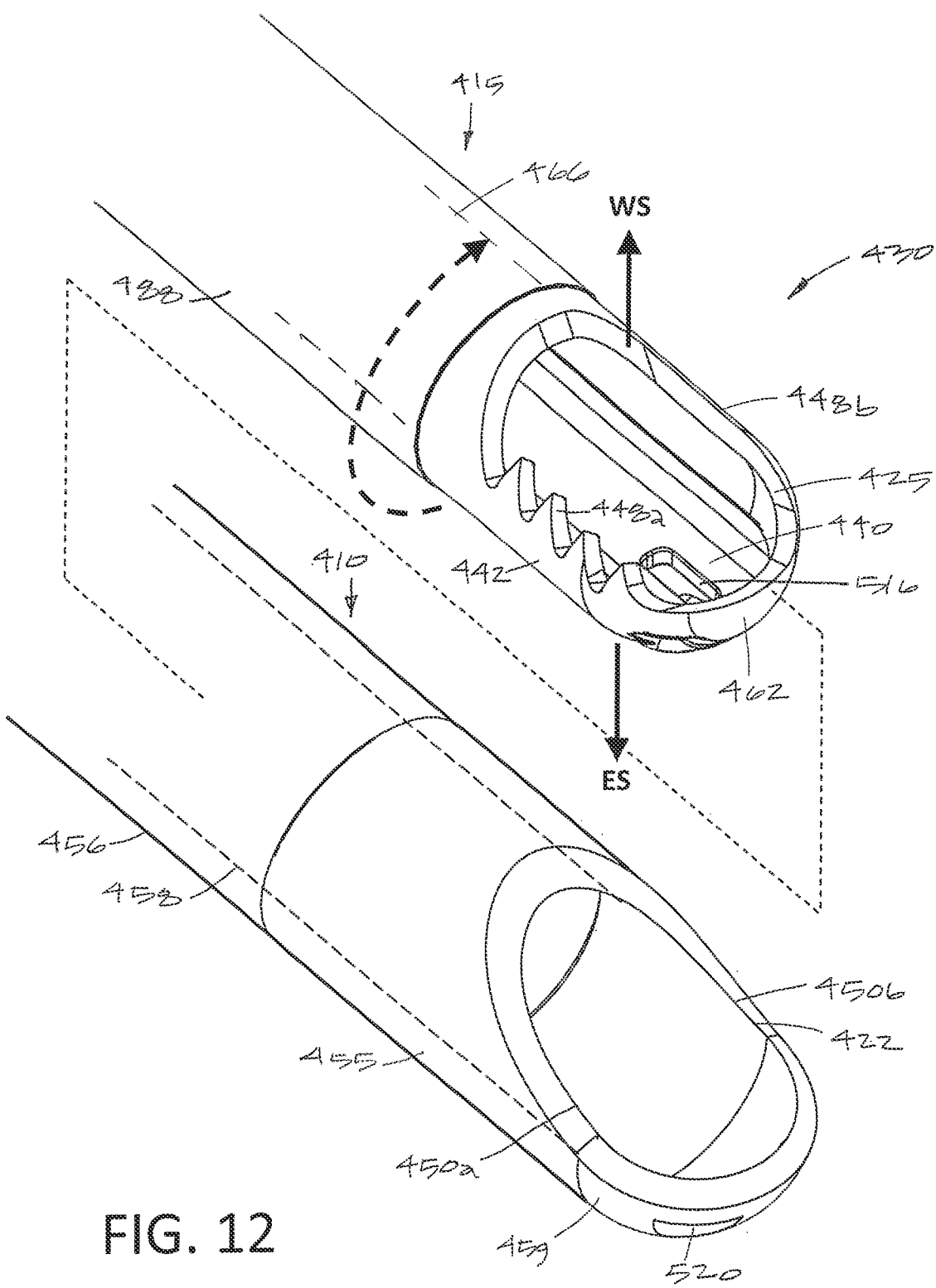
FIG. 12 is a perspective view of the working end as in FIG. 11 with the inner sleeve rotated 180°.

Now turning to FIGS. 10, 11 and 12, another variation of an arthroscopic shaver or resection probe 400 is shown which somewhat similar to that of FIGS. 12 and 3A-3B which comprises a tubular cutter having a proximal hub 402 coupled to an elongated shaft assembly 405 that extends about central longitudinal axis 406. The shaft assembly comprises an outer sleeve assembly 410 and a co-axial or concentric inner sleeve assembly 415 that extends to a shaft working end 418. The hub 402 again is adapted for coupling to a handpiece and motor drive controlled by a controller 420A. The controller 420A further controls the RF source 420B and negative pressure source 420C as described previously. The controller 420A includes algorithms having the features described in previous embodiments for rotating the inner sleeve assembly 415 as well as stopping the inner sleeve 415 in a selected rotational position, such as a window-closed or window-open position. The working end 418 again has an outer sleeve resecting window 422 in the outer sleeve assembly 410 that cooperates with an inner sleeve resecting window 425 (FIG. 12) in the inner sleeve assembly 415 for engaging and resecting tissue.

The variation or probe 400 in FIGS. 10, 11 and 12 differs from previous embodiments in that the inner sleeve assembly 415 has a distal end portion 430 that comprises a combination of a longitudinal dielectric member or body 440 coupled to a longitudinal conductive member or portion 442. The dielectric member 440 can be a ceramic or glass material and the longitudinal conductive portion 442 typically is stainless steel. When assembled, the dielectric member 440 and longitudinal conductive portion 442 have outer surface that contact one another along an interface 444 which is important for reasons described in more detail below.

As can be seen in FIG. 11, which shows components of the inner sleeve assembly 415 separated, the longitudinal dielectric member 440 carries an active electrode 445 which may be also may be referred to as a first polarity electrode herein. For convenience, the side of the inner sleeve assembly 415 that carries the electrode 445 is called the electrode side ES and the opposing side which carries inner window 425 is called the window side WS. Referring to FIG. 12, the inner sleeve resecting window 425 has circumferentially spaced-apart first and second cutting edges 448a and 448b that are sharp for mechanically resecting tissue as such cutting edges 448a, 448b shear tissue when rotating or rotationally oscillating across the cutting edges 450a and 450b of the outer sleeve window 422. Of particular interest, the longitudinal conductive metal portion 442 comprises a return electrode 455 (which also may be termed a second polarity electrode herein) which cooperates with the first polarity or active electrode 445 to deliver energy to tissue. The active and return electrodes 445 and 455 are operatively coupled to RF source 420B and controller 420A as described previously. The outer sleeve assembly 410 has a conductive metal outer tubular member 456 with bore 458 therein that extends proximally to the hub 402 and distally to the distal end portion or housing 459 that carries the outer sleeve window 422. The inner sleeve assembly 415 has a co-axial conductive metal inner tubular member 460 that extends proximally to the hub 402 and extends distally to couple to the assembly of the longitudinal dielectric member 440 and the longitudinal metal portion 442. The co-axial metal inner tubular member 460 rotates in the bore 458 of the outer tubular member 456.

As can be seen best in FIGS. 12 and 14, the longitudinal metal portion 442 has dual functions in that the carries the inner cutting window 425 with circumferentially spaced-apart first and second cutting edges 448a and 448b and also functions as a return electrode 455 when in a window-closed position of FIG. 10, as will be described further below.

Figure 15:
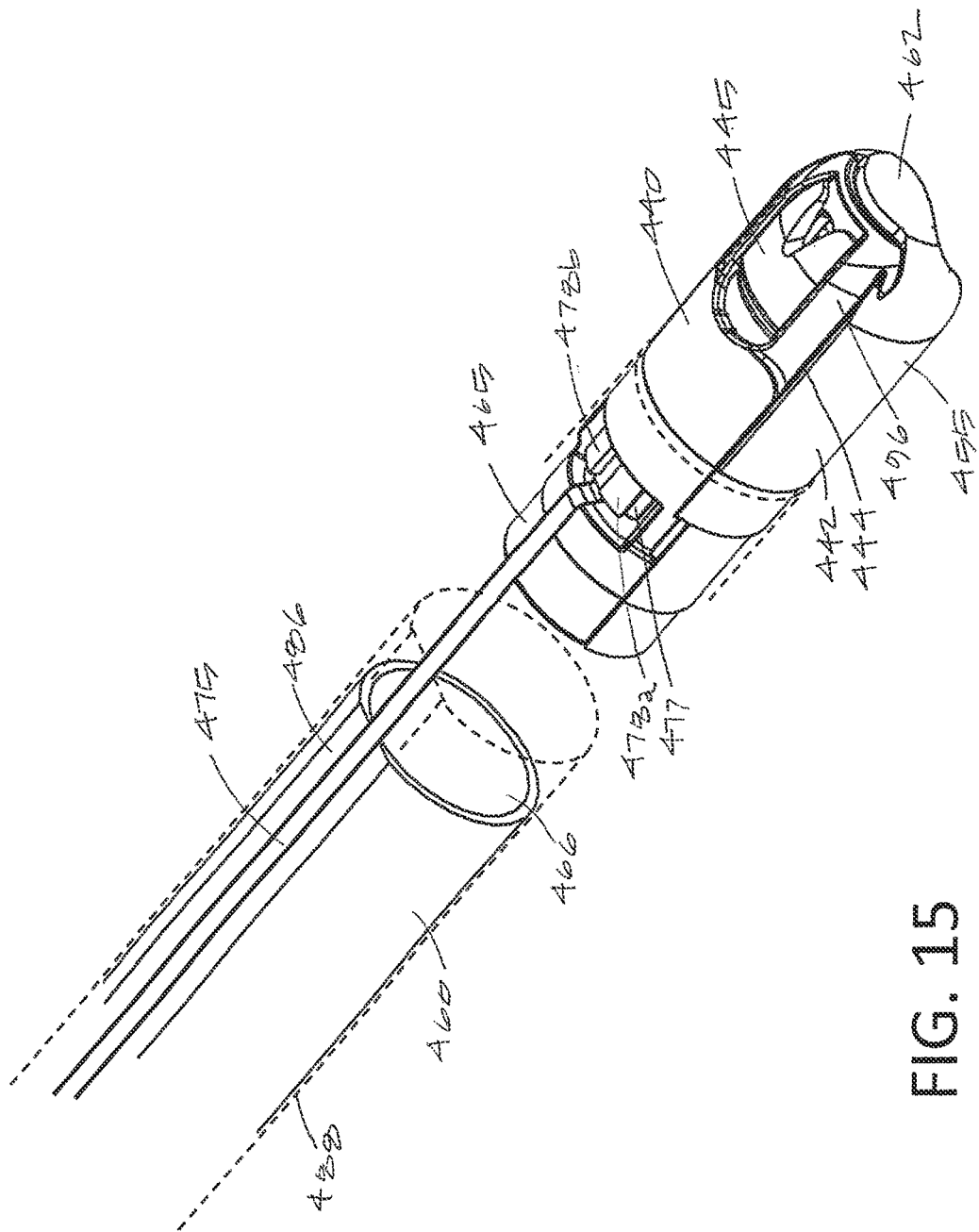
FIG. 15 is a perspective and partly assembled view of the working end of FIGS. 10-14 showing electrical connections therein.

Now referring to FIG. 12, the inner sleeve assembly 415 again is shown separated from the outer sleeve assembly 410 and is rotated 180° so that the electrode side ES faces downward and the window side WS is in an upward position. Thus, it can be seen that the longitudinal metal portion 442 carries the inner resecting window 425. Further, the longitudinal metal portion 442 extends distally around the tip portion 462 of the inner sleeve assembly 415 to thus provide substantial hoop strength as the tip portion 462 distally surrounds the longitudinal dielectric member 440 on opposing sides of the distal end 464 of the dielectric member 440. As can be seen in FIG. 15, the proximal end 465 of the assembly of the longitudinal dielectric member 440 and the longitudinal metal portion 442 is dimensioned for insertion into the bore 466 of the thin wall tubular sleeve 460 to complete the structural components of the inner sleeve assembly 415. Thus, it can be seen how the tubular sleeve 460 with bore 466 therein slides over and engages with the longitudinal dielectric member 440 and longitudinal metal portion 442 to provide a strong connection around the proximal end 465 of the components. As can best be seen in FIG. 13, the lateral sides 470a and 470b of the longitudinal dielectric member 440 are configured to slide into receiving recesses or grooves 472a and 472b on either side of the open channel 474 in the longitudinal metal portion 442 to thereby lock the two components 440 and 442 together.

Figure 13:
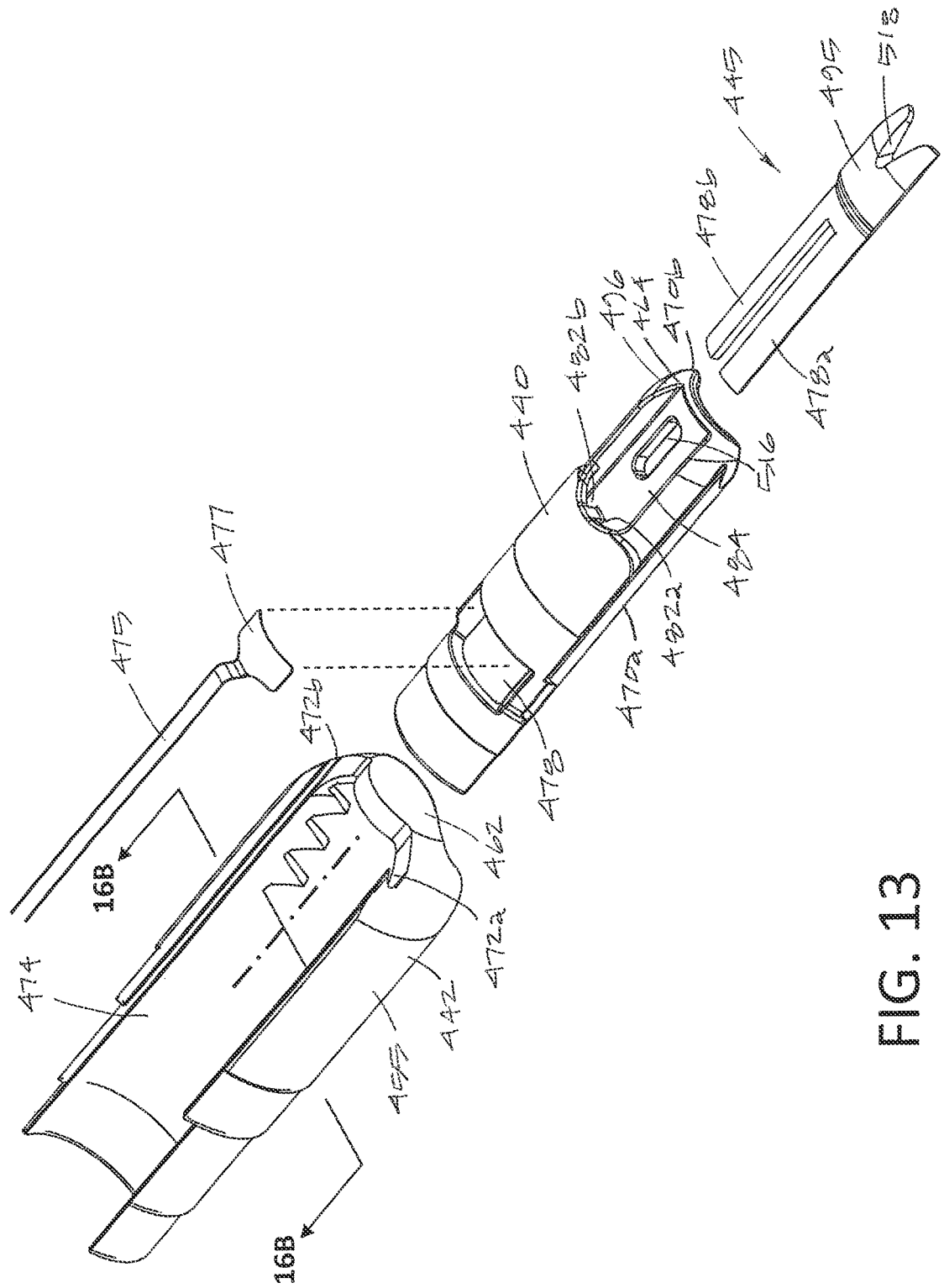
FIG. 13 is a perspective view of the working end of the probe of FIG. 10 in an exploded view showing the components thereof.
Figure 14:
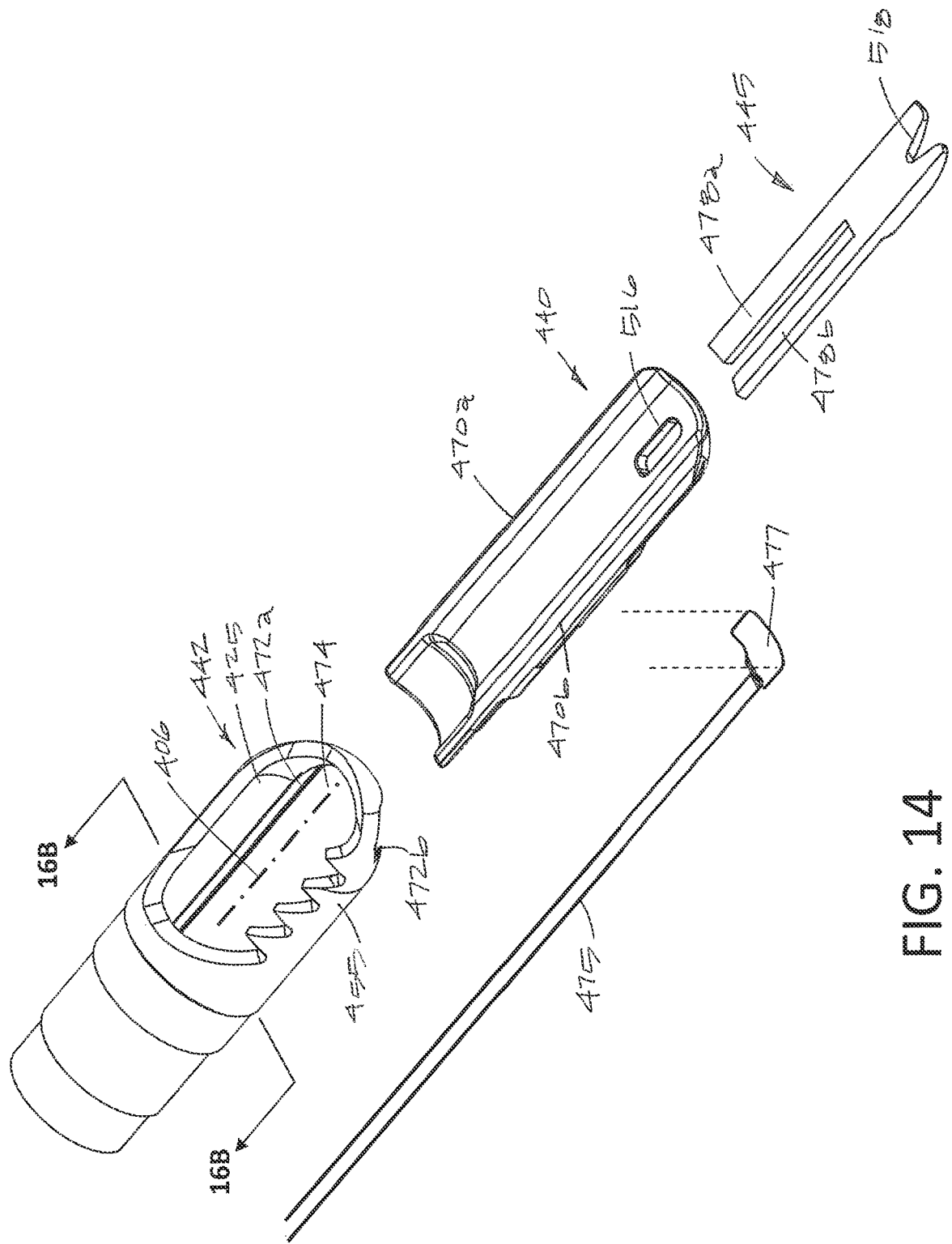
FIG. 14 is a perspective exploded view of the working end as in FIG. 13 rotated 180° to show another side of the components thereof.

FIG. 14 shows the exploded view of the components of FIG. 13 rotated 180° degrees to again show the lateral sides 470a, 470b of the dielectric member 440 configured for insertion into the receiving grooves 472a, 472b on either side of the channel 474 in the longitudinal metal portion 442.

Now turning to FIGS. 13 and 15, the electrical connections to the active electrode 445 and return electrodes 455 can be described. In the exploded view of FIG. 13, it can be seen that an elongated electrical lead 475 is adapted to extend longitudinally over the inner tubular member 460 (FIG. 15) to a pad portion 477 that is bendable and adapted to be inserted into a pad recess 478 in the longitudinal dielectric member 440. The electrical lead 475 is covered with an insulator (not shown) except for the pad portion 477. As can be easily understood, the active electrode 445 comprises a metal such as stainless steel, tungsten or any other suitable conductive metal with first and second legs 478a and 478b that are adapted for insertion through receiving channels 482a and 482b in the dielectric member 440 which extend into the pad recess 478. Thus, it can understood that the electrode 445 is cantilevered over a grooved portion 484 of the dielectric member 440 distally from the dual receiving channels 482a and 482b in the dielectric member 440. The pad 477 of the electrical lead 475 then is placed in the contact with the legs 478a and 478b of the electrode 445 and soldered or otherwise electrically coupled in the recess 478. Finally, a potting material (not shown) is used to cover and fill in over the electrical pad 477 and the recess 478. Further, referring to FIG. 15, it can be seen that tubular member 460 has a flattened surface 486 for accommodating the electrical lead 475 as the tubular member 460 and bore 466 therein slide over the proximal end 465 of the dielectric member 440 and metal portion 442. The flattened surface 486 of the tubular member 460 as seen in FIG. 15 allows an insulator layer 488 (such as a heat shrink material) shown in phantom view to cover the entirety of the tubular member 460, the insulated electrical lead 475, and the proximal and medial portions 465, 490 of the dielectric member 440 and the longitudinal metal portion 442. This describes the electrical lead 475 extending to the active electrode 445 carried within the dielectric member 440. The proximal end (not shown) of the electrical lead 475 extends into the hub 402 (FIG. 10) and thereafter connects to electrical contacts in a handle which allows for rotation of the inner sleeve assembly 415 and for coupling electrical energy to the electrical lead 475, as described in earlier embodiments.

As described above, the longitudinal metal portion 442 of the inner sleeve assembly 415 (FIGS. 13, 15) comprises a return electrode 455. However, the inner sleeve assembly 415 does not carry electrical lead to the longitudinal metal portion 442. Rather, the outer sleeve assembly 410 of FIGS. 10, 11 and 12 includes an elongate metal outer tubular member 456 that comprises an electrical conductor and is adapted to carry current from the hub 402 to the distal end or housing portion 459 of the outer sleeve assembly 410. Since the longitudinal metal portion 442 of the inner sleeve assembly 415 rotates with a close fit within the bore 458 of the outer tubular member 456, the longitudinal metal portion 442 becomes a return electrode 455 due to its contact with the outer tubular member 456. Thus, referring to FIG. 12, the longitudinal metal conductive portion 442 and the distal end housing 459 of the outer tubular member 456 both comprise a return electrode 455.

Figure 16A:
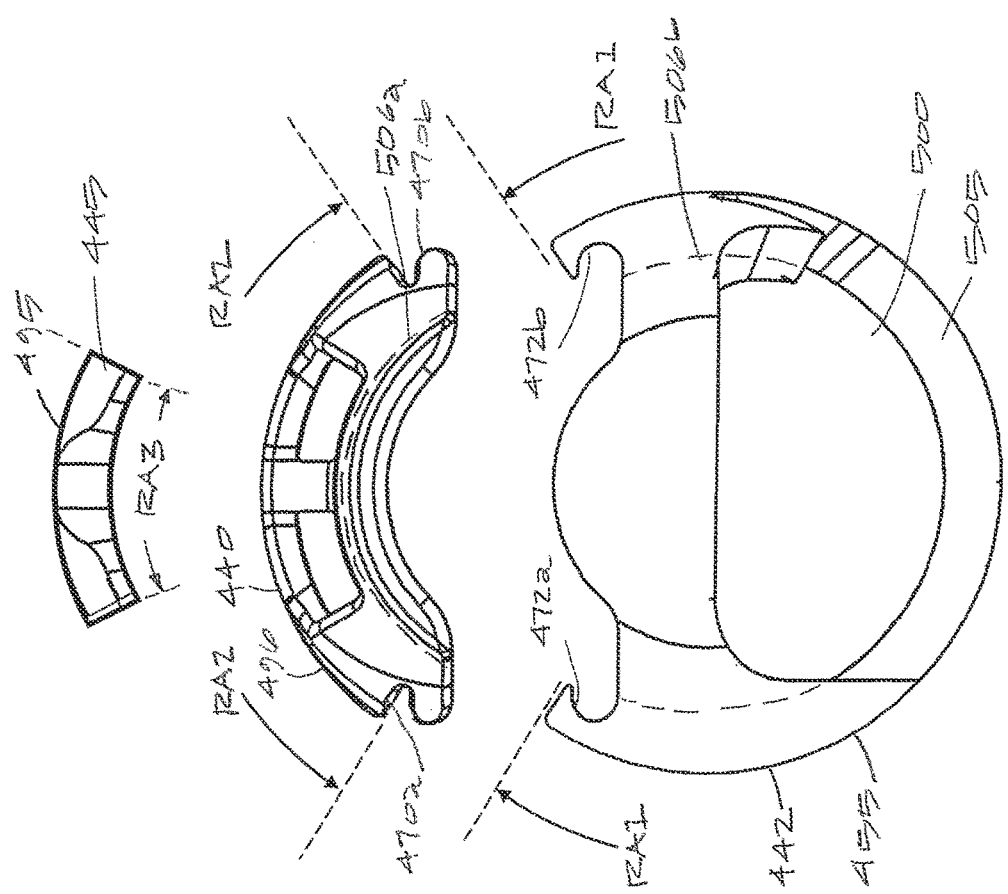
FIG. 16A is an end view of components of the working end of FIGS. 10-15.

In another aspect of the invention, referring to FIGS. 15 and 16A, the active electrode 445 is dome-shaped with a surface 495 that has a radius or curvature that is a segment of a cylindrical shape so that the outer surface 495 of the dome of the electrode 445 when viewed in a transverse sectional view (FIG. 16A) is substantially aligned with the outer cylindrical surfaces 496 of the dielectric member 440 and longitudinal metal portion 442. The dome-shaped surface 495 of the electrode 445 is advantageous for engaging tissue since it projects outward as opposed to a flat-surface electrode. Further, the thicker, dome-shaped central portion of electrode 445 results in far slower degradation and disintegration of the electrode 445 during prolonged use. Such electrode durability is important for arthroscopic procedures in which the electrosurgical components of the invention may be used for many minutes.

Referring again to FIGS. 16A-16B, in one aspect of the invention, the longitudinal dielectric member 440 together with the longitudinal metal portion 442 form a wall around an interior channel 500 therein that communicates within bore 466 in the inner tubular member 460 and a negative pressure source 420C for aspirating tissue chips and fluid from a working space as is known in the art. In one variation shown in FIGS. 16A-16B, the metal wall portion 505 (disregarding the opening of window 422 therein) extends radially around axis 406 and the interior channel 500 in a radial angle RA1 of at least 90°. Often, the metal wall portion 505 will extend radially around the interior channel in a radial angle RA1 of at least 120° or at least 180°. When describing the metal wall portion 505 herein that extends in a radial angle indicated at RA1 in FIGS. 16A-16B, it is meant to refer, for example, to the metal wall portion 505 of FIG. 16B which is a transverse section 16B-16B in FIGS. 13-14 which is proximal to window 425, where such a wall portion 505 provides the required hoop strength to the metal portion 442. In this variation, referring to FIGS. 16A-16B, the wall 510 of the dielectric member 440 extends radially around the interior channel 500 in a radial angle RA2 of at least 45° or at least 60°. Further, still referring to FIG. 16A, the dome-shaped electrode 445 has a surface 495 that extends radially around the axis 406 in a radial angle RA3 of at least 5° or at least 10°.

Figure 17:
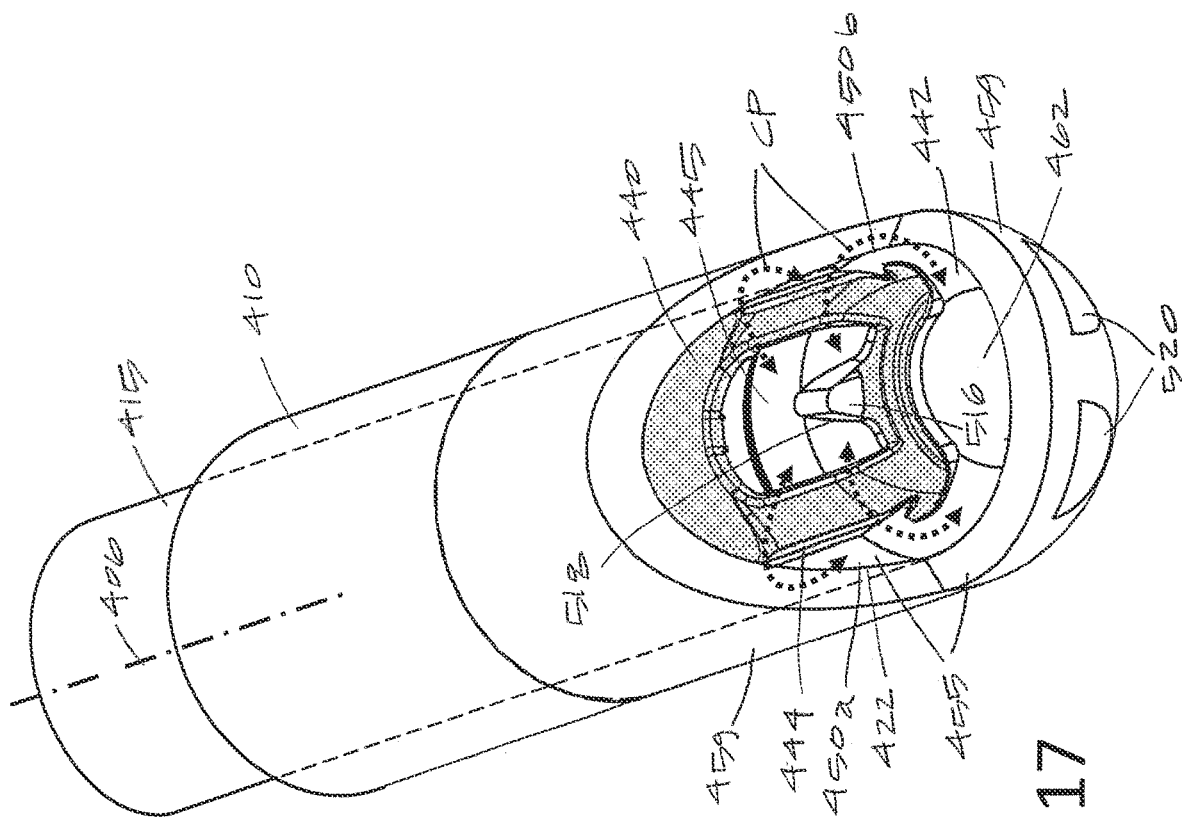
FIG. 17 is a perspective view of the working end of FIGS. 10-15 showing RF current paths between active and return electrodes.

Now turning to FIG. 17, another important aspect of the invention can be described. As can be seen in FIG. 17, the inner sleeve assembly 415 has been stopped in a selected rotational position wherein the electrode 445 carried by the dielectric member 440 is positioned centrally in the resecting window 422 of the outer sleeve assembly 410. In this variation, it should be appreciated that the outer sleeve window 422 is shown with sharp metal cutting edges without teeth or serrations, but it should be appreciated that the outer sleeve window 422 can have any form of sharp teeth, serrations or the like and fall within the scope of the invention.

In FIG. 17, it can also be seen that the longitudinal metal portion 442 of the inner sleeve assembly 415 is exposed in the outer sleeve window 422 when the outer sleeve assembly 415 has been stopped in the rotational position where electrode 445 is positioned centrally in the resecting window 422. As described above, both the distal portion or housing 459 of the outer sleeve assembly 410 and the longitudinal metal portion 442 of the inner sleeve assembly 410 comprises return electrodes 455. FIG. 17 shows RF current paths CP that indicate the shortest path for RF current between the active electrode 445 and the return electrode 455 when operating in conductive saline environment. As can be seen in FIG. 17, the shortest RF current paths CP are from the active electrode 445 to the longitudinal metal portion 442 along interface 444 of the dielectric member 440 and metal portion 442 and not the cutting edges 450a and 450b of the outer window 422 in distal housing 459 which comprise the return electrode 455. This aspect of the invention is very important in that the location of the interface 444 between the dielectric member 440 and metal portion 442 is critical to prevent a short current path CP to the cutting edges 450a and 450b of outer window 422. If substantial RF current path were directly from electrode 445 to cutting edges 450a and 450b, the RF plasma at the cutting edges would rapidly degrade and dull such edges. In turn, the dull cutting edges of the outer sleeve window 422 would diminish the resection rate resulting from rotating or oscillating the inner sleeve assembly 415 and window 425 in the outer sleeve window 422.

In general, a surgical a probe for resecting tissue corresponding to the invention (FIGS. 10-17) comprises an elongated shaft extending about a longitudinal axis 406 comprising co-axial outer and inner sleeve assemblies 410, 415 having respective outer and inner resecting windows 422 and 425 in distal ends thereof, wherein the inner sleeve assembly has (i) a longitudinal dielectric wall portion that carries a first polarity or active electrode 445, and (ii) a conductive metal wall portion with an inner resecting window 425 with circumferentially spaced-apart first and second conductive cutting edges 448a and 448b that comprise a return electrode 455, wherein the active electrode 445 is spaced apart from the cutting edges 448a, 448b by at least 0.5 mm. An RF source 420B coupled to the active and return electrodes. In other variations, the first and second polarity electrodes 445, 455 (or active and return electrodes 445, 455) are spaced apart by at least 1.0 mm or at least 1.5 mm. In a variation, the dielectric member 440 defines a longitudinal interface 444 with a longitudinal edge of an conductive longitudinal metal portion 442 which comprising a second polarity or return electrode.

In general, referring to FIG. 17, a tissue resecting probe corresponding to the invention comprises an elongated shaft 405 extending about a longitudinal axis 406 and further comprises co-axial outer and inner sleeve assemblies 410 and 415 having respective outer and inner resecting windows 433 and 425 in distal ends thereof, wherein inner sleeve assembly 415 carries a first polarity electrode 445 therein, and both the outer and inner windows 422 and 425 have circumferentially spaced-apart cutting edges that comprise second polarity electrodes.

In another aspect of the invention, again referring FIG. 17, the surgical resecting probe comprises a windowed inner sleeve assembly 415 rotatable within a windowed outer sleeve assembly 410 wherein a controller 420A and motor drive are adapted to rotate the inner sleeve assembly through window-open and window-closed positions and wherein the controller is adapted to stop motor-driven rotation of the inner sleeve assembly in a selected position wherein the active electrode 445 is spaced apart from cutting edges 450a and 450b of the outer sleeve window 422 and wherein a return electrode 455 is disposed intermediate the electrode 445 and the cutting edges 450a and 450b of the outer sleeve window 422.

Figure 16B:
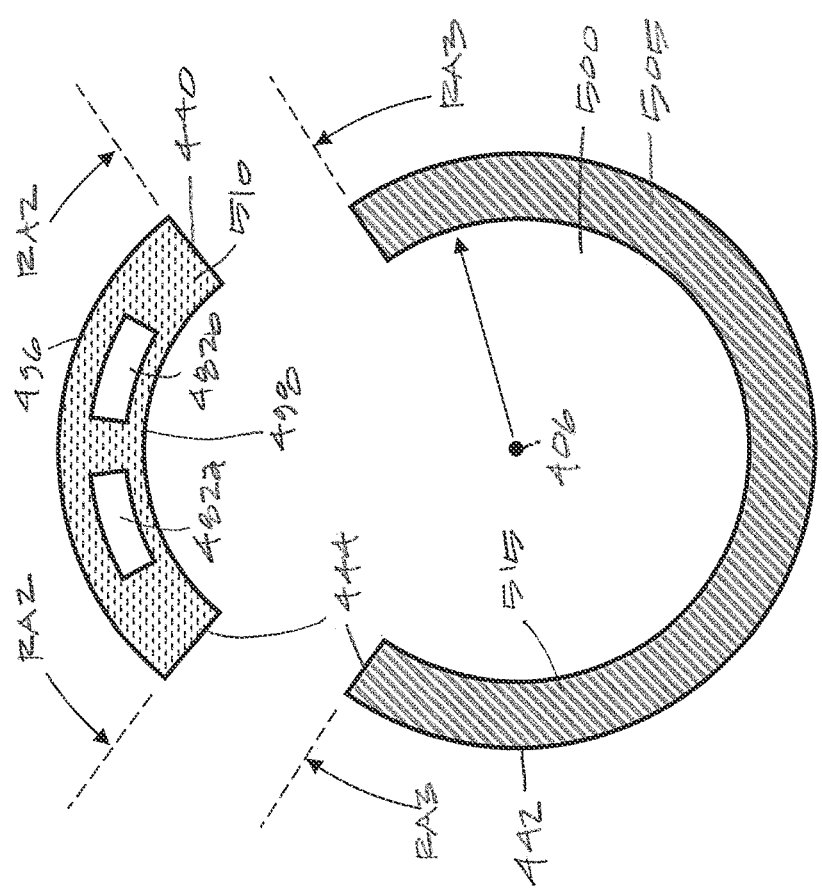
FIG. 16B is a cross-sectional view of components of the working end of FIGS. 10-15 taken along line 16B-16B of FIG. 13.

In another aspect of the invention, referring to FIGS. 13 and 16, the resecting probe 400 comprises a windowed inner sleeve assembly 415 rotatable within a windowed outer sleeve assembly 410 wherein a controller and motor drive are adapted to rotate the inner sleeve assembly 415 through window-open and window-closed positions, wherein a distal portion of the inner sleeve assembly 415 comprises a cylindrical wall defining an outer surface 496 and an inner surface 498 around an interior channel 500 therein (FIG. 16B) and wherein the interior channel 500 is surrounded in part by a first wall 510 of the longitudinal dielectric member 440 and in part by a second wall 515 of the longitudinal metal portion 442 and wherein each of the first and second walls 510 and 515 comprise substantially the full thickness of the cylindrical wall and is not a thin layer of a composite or layered assembly. Again, it should be appreciated that the term second wall 515 as used herein describes the wall structure proximal to the window 425 which is disposed in the longitudinal metal portion 442.

In FIGS. 10-15, it can be seen that the dielectric member 440 has a port 516 therein that lies under a v-notch 518 in the electrode 445. The port 516 is adapted for aspiration of fluid therethrough during RF energy delivery which can reduce bubbles from the vicinity of the electrode 445 as plasma is formed. Further, FIGS. 10 and 17 show ports 520 in the distal end housing 459 of outer sleeve 410 which are adapted to provide fluid flow through the shaft assembly in a window-closed position as shown in FIGS. 10 and 17 to maintain a constant fluid outflow as opposed to a fluctuating outflow as would be the case otherwise with the inner sleeve assembly 415 rotating at high RPM through window-open and window-closed positions.

Figure 18:
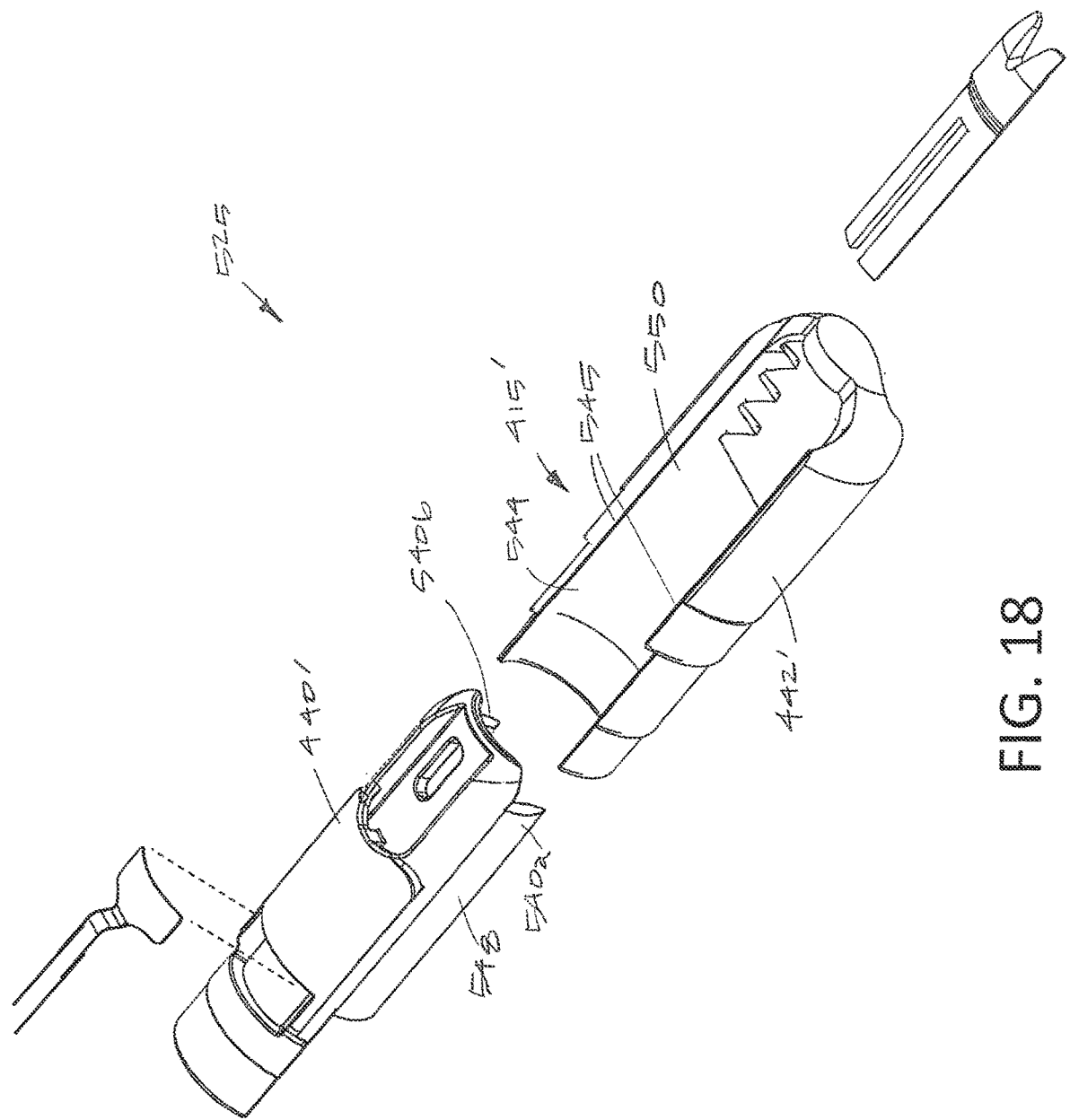
FIG. 18 is a perspective exploded view of a working end of another variation of a probe similar to that of FIG. 10 showing the components thereof.
Figure 19:
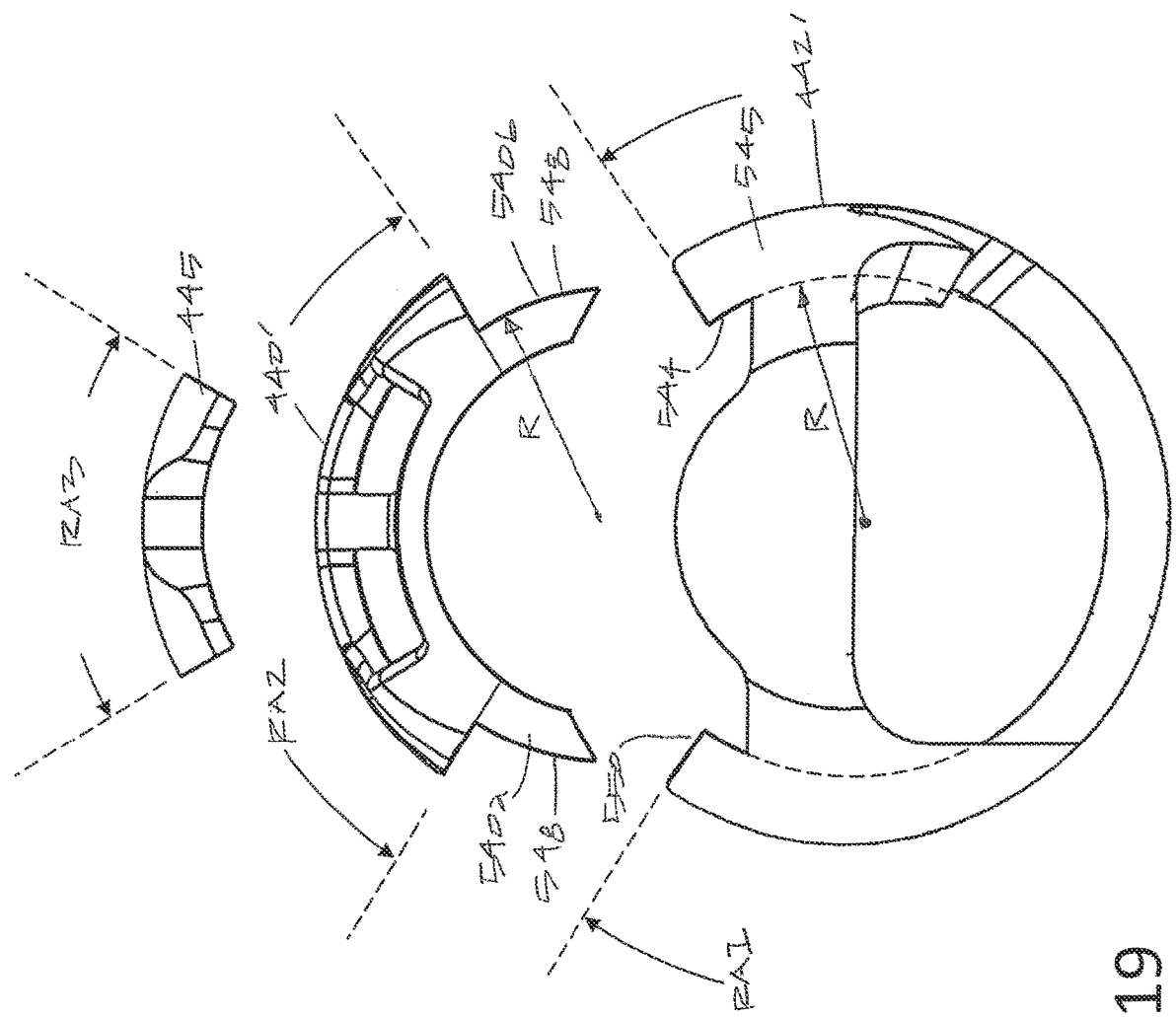
FIG. 19 is an end view of components of the working end of FIG. 18.

Now turning to FIGS. 18-19, another variation of a probe working end 525 is shown, and more particularly the distal end of the inner sleeve assembly 415' is shown in an exploded view and is similar to the embodiment of FIGS. 10 to 16. The variation of FIG. 18 again includes a longitudinal dielectric body 440' and a longitudinal conductive metal body 442'. This variation differs the previous embodiment shown in FIG. 13 in that the structure provided for securely coupling the components 440' and 442' together differs. As can be seen in FIGS. 18 and 19, the dielectric component 440' has lateral elements 540a and 540b extending in a part-cylindrical form that are adapted to slide into and engage the inner surfaces 544 of walls 545 of the metal longitudinal metal body portion 442'. As best can be seen in FIG. 19, the lateral elements 540a and 540b of the dielectric member 440' have an outer surface 548 with a radius R that matches the inner surface 544 and radius R of the metal portion 442'. Thus, it can be understood that by axially sliding and inserting the dielectric member 440' can into the longitudinal opening or channel 550 in longitudinal metal portion 442', a secure and durable connection can be provided between the dielectric and metal components 440' and 442'. In FIG. 19, the radial angle RA1 of the metal portion 442' and the radial angle RA2 of the dielectric member 440' can be the same as described previously. Additionally, the radial angle RA3 of the surface of the electrode 445 is the same as described previously.

Figure 20:
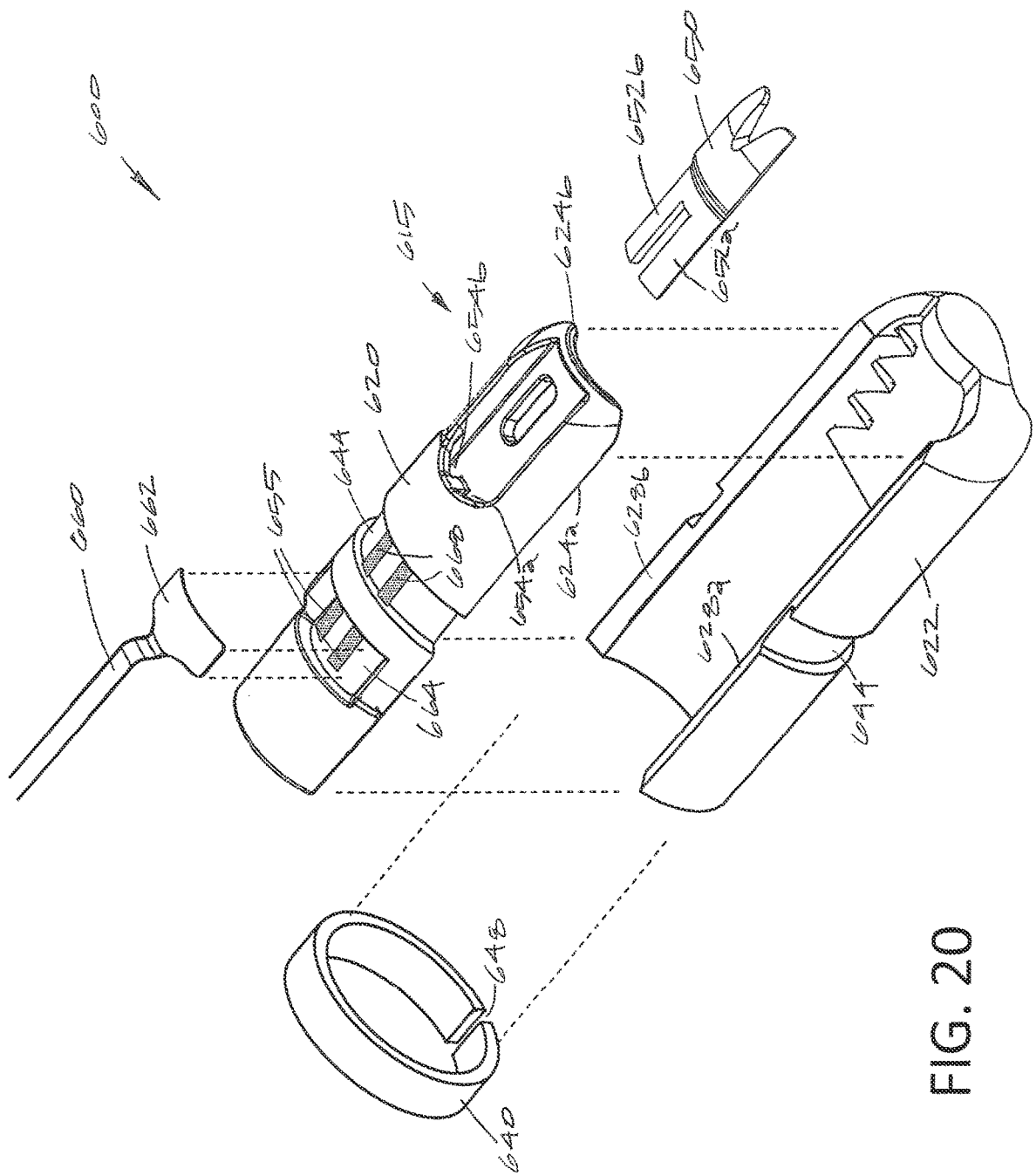
FIG. 20 is a perspective exploded view of another variation of a probe similar to that of FIGS. 10 and 18 showing the components thereof.
Figure 21:
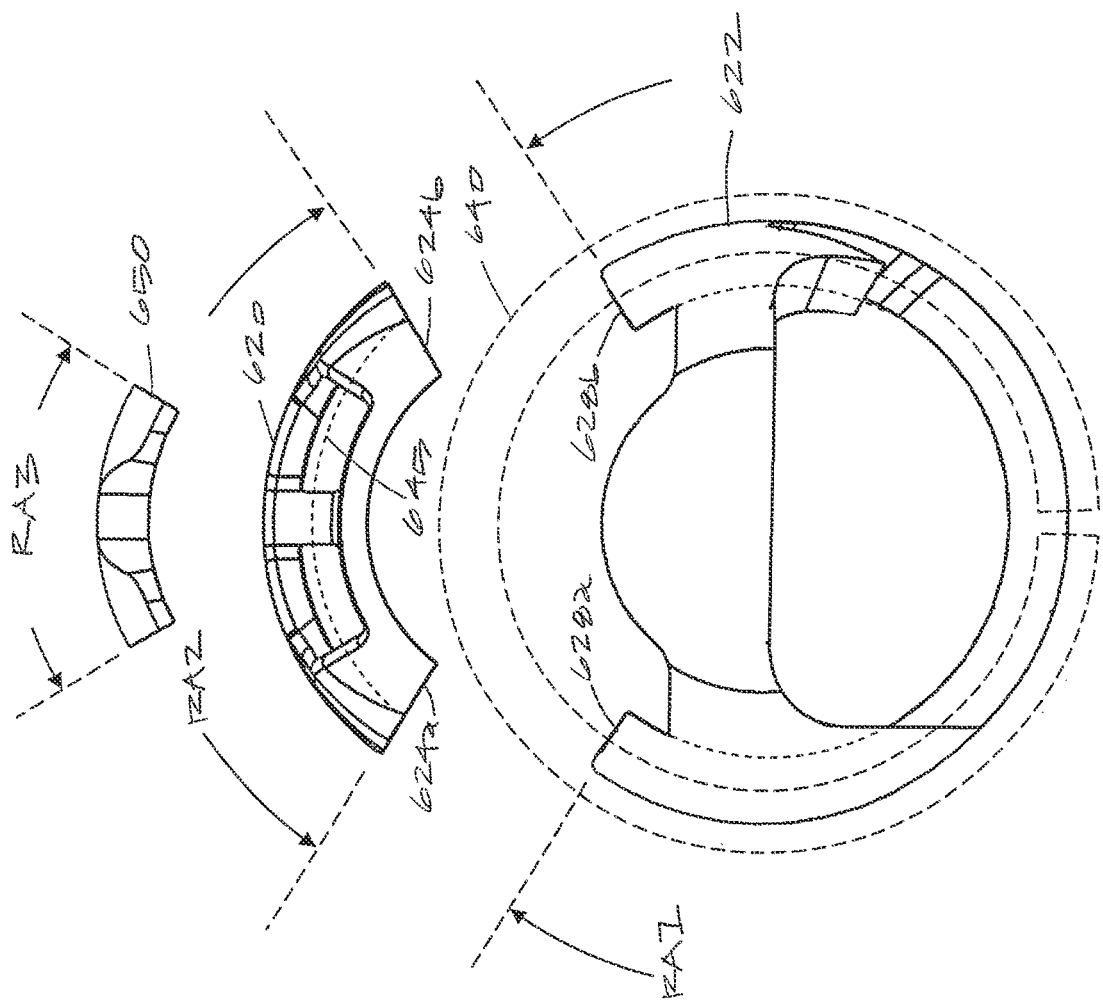
FIG. 21 is an end view of components of the working end of FIG. 20.

In FIG. 20, another variation of a working end 600 of an inner sleeve assembly 615 is provided in an exploded view to illustrate the structural components that are adapted to securely connect the longitudinal dielectric member 620 to the longitudinal metal portion 622. In this variation, the lateral edges 624a and 624b of the dielectric member 620 do not interlock with the lateral edges 628a and 628b of the metal portion 622 or overlap as in the previous variations. As can be seen in FIGS. 20 and 21, the interfaces of the lateral edges of the components 620, 622 simply abut one another and are securely fixed to one another by a retaining collar 640 that is adapted to fit into an annular notch or recess 644 in both the dielectric member 620 the metal portion 622 to securely hold the components together. As can be understood, the metal retaining collar 640 can have a discontinuity or gap 648 in its circumference to allow the collar to be tensioned and slipped over the components 620 and 622 into the recess 644. Thereafter, the gap 648 in the collar 640 can be welded to thus permanently couple the dielectric and metal components 620 and 622.

In the variation shown in FIG. 20, it can be seen that an active electrode 650 with legs 652a and 652b is similar to the version described previously in FIGS. 13-15. In FIG. 20, it can be seen that the legs 652a and 652b extend into receiving channels 654a and 654b in the dielectric member 620. The electrical lead 660 in FIG. 20 again has a pad element 662 that is received by a recess 664 in the dielectric member 620 to contact electrical leads 665 therein. In this variation, the electrical leads 655 in the recess 664 are bare to make electrical contact with the pad element 662 but are coated with an insulator 668 is the location where such leads extend through the dielectric member 620 and into contact with the legs 652a and 652b of the electrode 650. In all other respects, the assembly of components in FIG. 20 functions in the same manner as described previously. In FIG. 21, it can be seen that the radial angles RA1, RA2 of the walls of the metal member 622 and dielectric member 620 can be the same as described previously. Additionally, the radial angle RA3 of the surface of the electrode 650 is the same as described previously.

Figure 22:
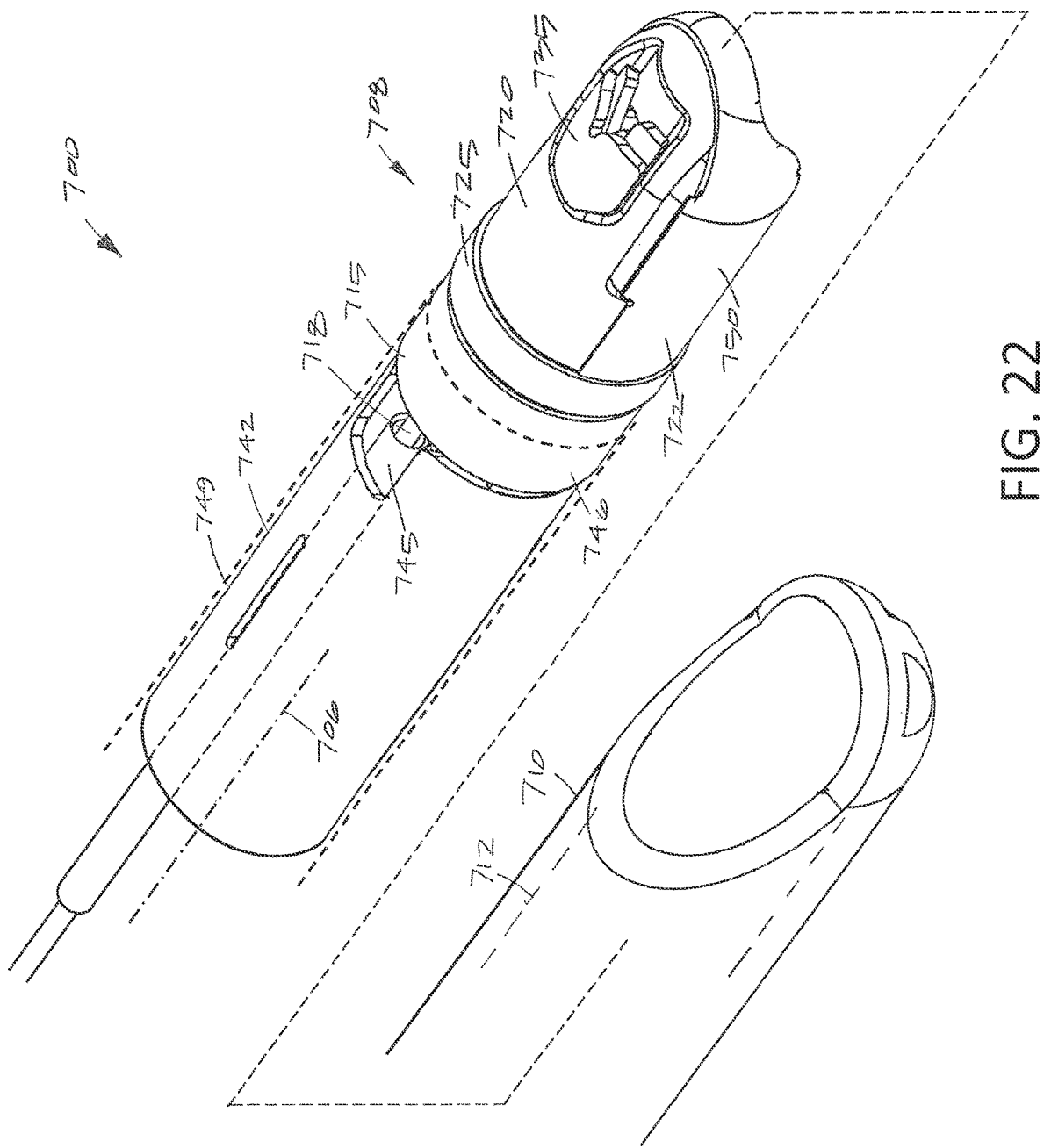
FIG. 22 is a perspective partly disassembled view of another variation of a probe similar to that of FIGS. 10 and 18 showing the components thereof.
Figure 23:
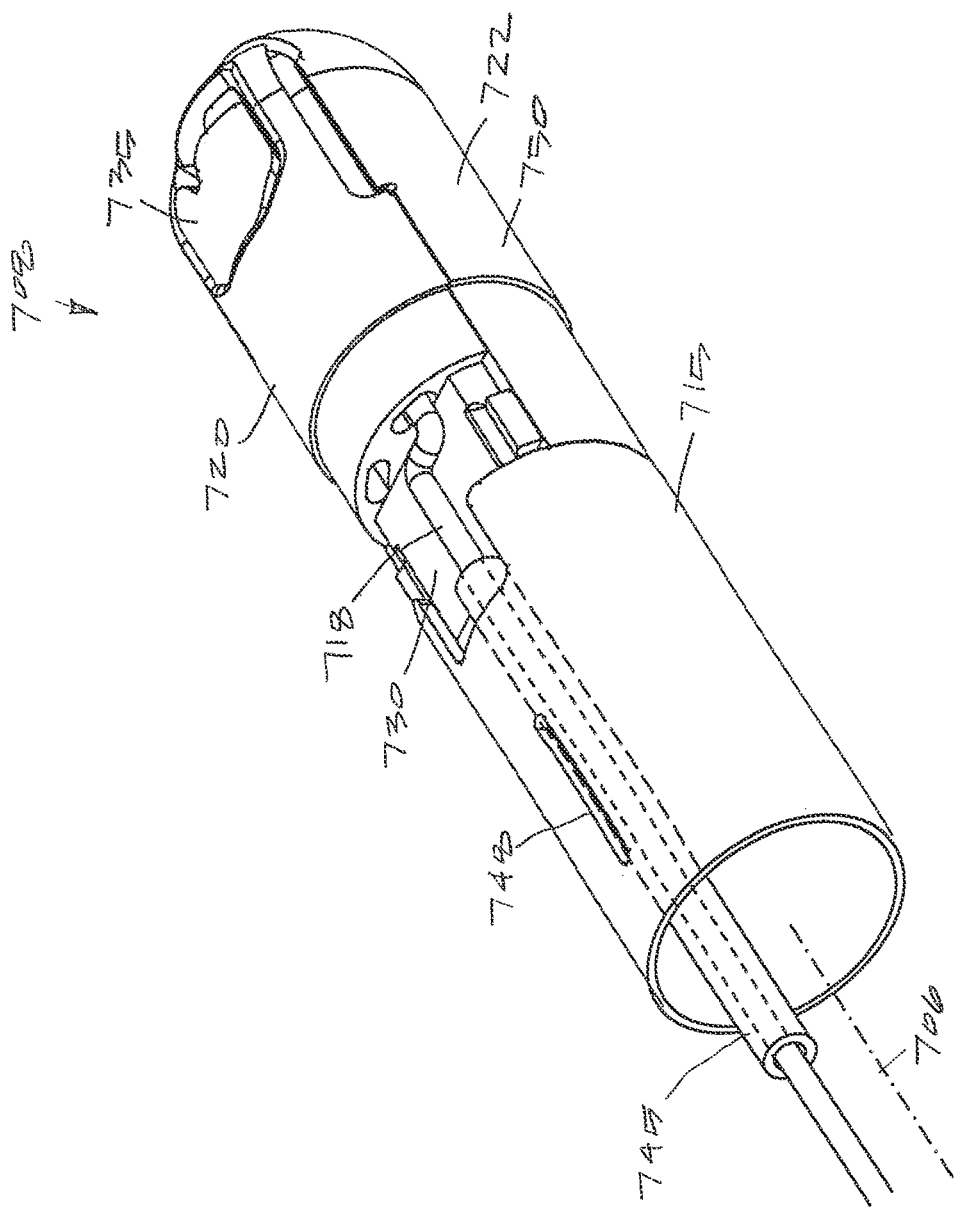
FIG. 23 is another perspective view of components of the working end of FIG. 22.

Now turning to FIGS. 22-26, another variation of probe 700 is shown with hub 702 and shaft 705 (see FIG. 25A) extending about longitudinal axis 706 to a working end 708 shown in FIG. 22. FIG. 22 shows a distal portion of the outer sleeve assembly 710 and bore 712 therein together with inner sleeve assembly 715. FIG. 23 shows the inner sleeve assembly 715 from a different angle to better illustrate the electrical lead 718 carried by the inner sleeve. Now turning to FIG. 24 which is an exploded view of the inner sleeve assembly 715, it can be seen that the longitudinal dielectric member 720 is again secured to the longitudinal metal portion 722 and coupled to tubular member 724 with a retaining collar 725. Such a retaining collar 725 used to fix together the dielectric member 720 and the metal portion 722 can be similar to that described in the embodiment of FIG. 20.

Figure 24:
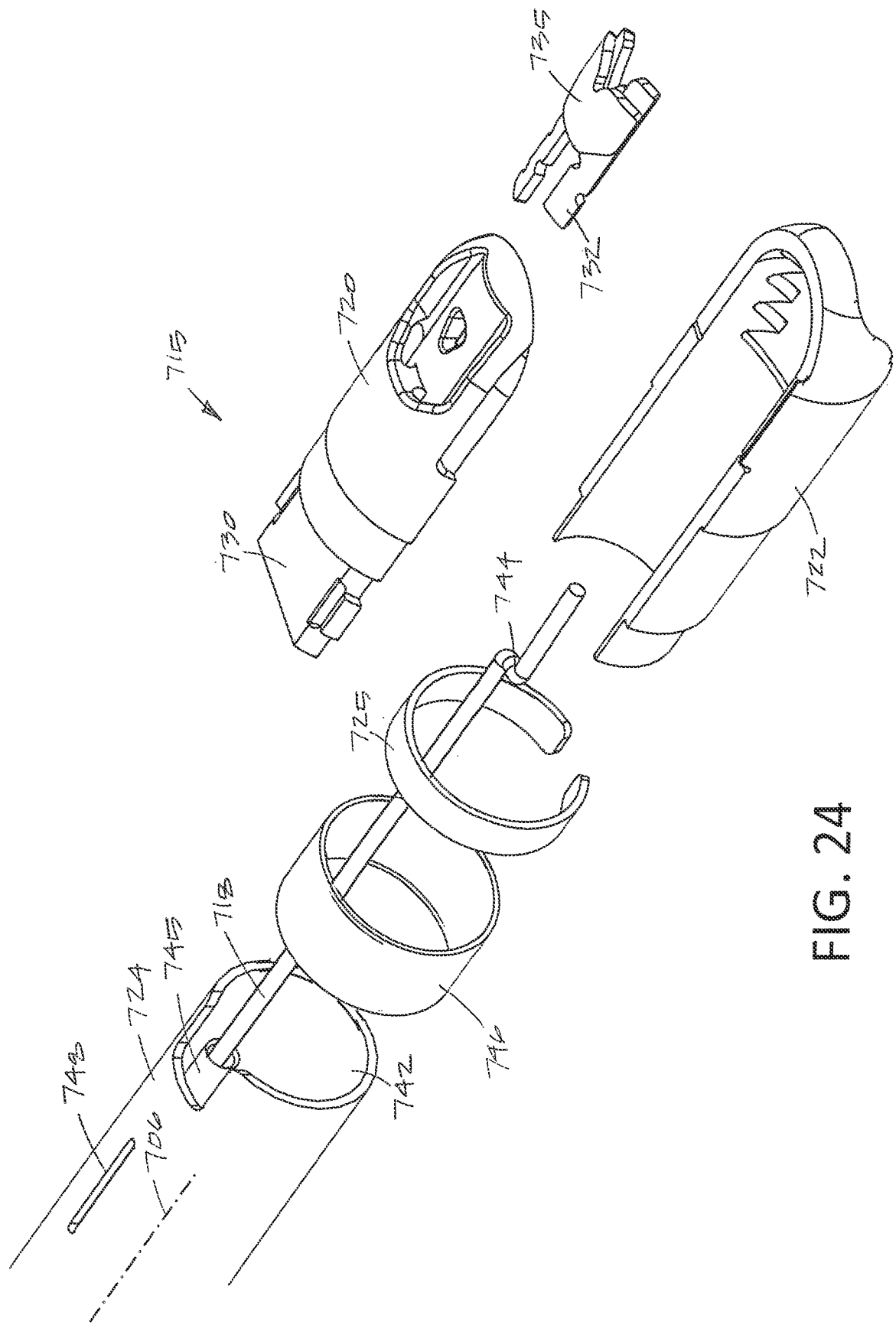
FIG. 24 is an exploded view of the component of the probe of FIGS. 22 and 23.

Referring to FIG. 24, this variation differs from previous embodiments in that the electrical lead 718 extends through a recess 730 in the dielectric member 720 and couples to a leg 732 of the active electrode 735. The electrical lead 718 is not carried on an exterior surface of tubular member 724. Instead, the electrical lead 718 extends to the active electrode 735 through the interior bore 742 of the tubular member. As can be seen in FIG. 22, the electrical lead 718 extends in the proximal direction from the electrode 735 and is flexed at bend 744 to enter the interior bore 742 of the inner tubular member 724 and in this variation extends through a hypotube 745 which is coupled to the wall of the tubular member 740. It can be seen that a slot 748 is provided in the wall of and tubular member 724 which allows for welding the hypotube 745 to the interior surface of bore 742 in the tubular member 724. At least one similar slot (not shown) can be provided along the length of the tubular member 724 to secure the hypotube 745 in place. It has been found that is important to carry the electrical lead 718 within the interior bore 742 of the tubular member 724 to protect it from potential damage. In the previous embodiments, for example the version of FIG. 15, the electrical lead 475 extended in a flat surface 486 along the outer surface of the inner tubular member 460 and was then covered with insulator layer 488. In the previous embodiment of FIG. 15, since the shaft 405 of the probe 400 (FIG. 10) could be torqued and bent significantly during a procedure, high-speed rotation of the inner sleeve assembly 415 had the potential of abrading and degrading the insulator sleeve 488 overlying the electrical lead 425 which could cause an electrical short. Therefore, one aspect of the invention as shown in FIGS. 22-24 includes carrying the electrical lead 718 in the interior bore 742 of the metal tubular member 724 to insure that bending or torque on the shaft 705 while operating the inner sleeve assembly 715 at high RPM cannot damage the electrical lead 718. FIGS. 22 and 24 also show an annular bushing 746 that is adapted to cover the recess 730 that is filled with potting material as described previously. Referring again to FIG. 22, a heat shrink insulator sleeve 748 covering the tubular member 724 and the at least a portion of the bushing 746. Thus, in high speed rotation, the insulator sleeve 749 and bushing 746 are the bearing surfaces of the inner sleeve assembly 715 as it rotates in the outer sleeve 710.

It can be appreciated from FIGS. 22-24 that the inner tubular member 724 and the hypotube 745 comprise a return electrode 750 with conductive saline flowing through the interior channel 755 of the tubular member 724. Thus, obviously the electrical lead 718 carries its own substantial insulation layer on it surface. In one variation, the electrical lead 718 is a copper wire instead of a stainless steel wire since such a stainless steel wire would be resistively heated. Preferably, the electrical lead 718 is of a material that will not be resistively heated as this would heat saline outflows traveling through the channel 755 which would then elevate the temperature of the handpiece which is undesirable.

Figure 26:
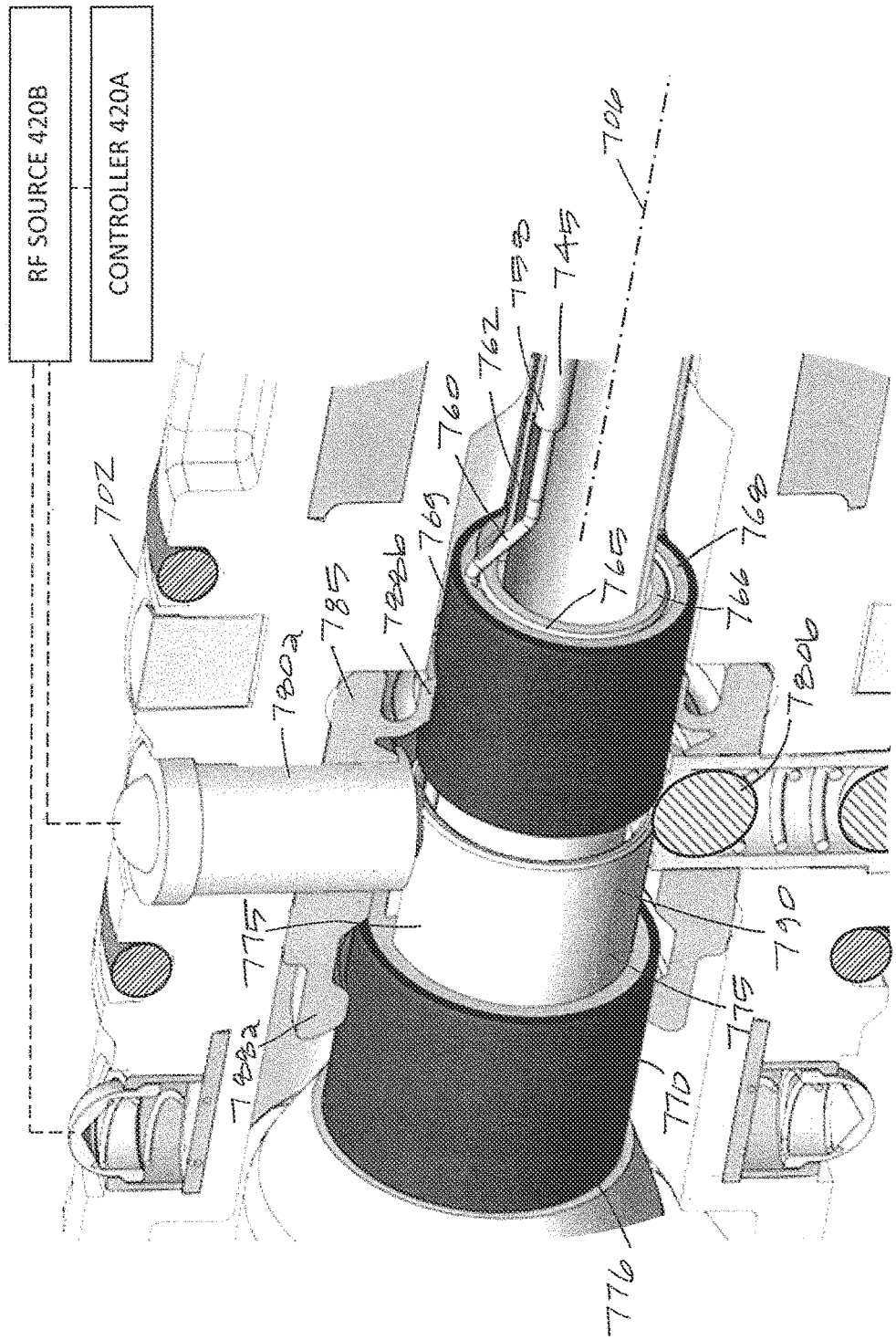
FIG. 26 is an enlarged sectional view of a portion of the hub of the probe of FIG. 25B.

Now turning to FIGS. 25A and 25B, a perspective view and a cut-away view of the hub 702 are shown. FIG. 26 is an enlarged cut-away view of an interior portion of the hub 702. As can be seen in FIGS. 25B and 26, the hypotube 745 carries the electrical lead 718 that extends through the inner tubular member 724. As can be seen in FIG. 25B, the tubular member 724 extends through the hub 702 and the hypotube 745 has a proximal end 758 in the interior of the hub. The proximal end portion 760 of the electrical lead 718 is curved outwardly through a slot 762 in the tubular member 724 and then extends in an interface 765 between two polymer collars 766 and 768 that together provide a seal over and around the insulation layer on the electrical lead 718. Thereafter, a heat shrink material 769 such as FEP can disposed over the collars 766 and 768 (FIG. 26). In FIGS. 25B and 26, it can be seen that a polymeric coupling sleeve 770 is fixed to the proximal end portion 772 of the tubular member that extends proximally to the drive coupler 774 which is adapted for coupling to the motor drive of the handpiece (not shown). FIGS. 25B and 26 further show conductive metal contact ring 775 is disposed over the insulative coupling sleeve 770. As can be seen in FIG. 26, on the proximal side of the contact ring 775, another polymeric collar 776 is shown that again is covered with an FEP or other heat shrink material. Still referring to FIG. 26, the proximalmost end 777 of electrical lead 718 with its insulator layer removed is in contact with and electrically coupled to the rotating contact ring 775. In turn, the contact ring 775 interfaces with spring-loaded ball contacts 780a and 780b in the handpiece (not shown) to carry RF current to from RF source 720B to the active electrode 735 (FIG. 22). Spring-loaded ball contacts 782a and 782b in the hub are adapted to carry current to or from the outer sleeve assembly 710 which comprises a return electrode. It should be appreciated that conductive fluid can migrate into various parts of the hub 702 and it is necessary to prevent any migration of conductive fluid into the interface between the spring-loaded ball contacts 780a and 780b and the rotating contact ring 775. Any migrating conductive fluid is effectively a return electrode and could cause a short circuit. To insure that there is no migration conductive fluid into contact with contact ring 775, FIGS. 25B and 26 illustrate a flexible seal 785 that has is flexible annular sealing elements 788a and 788b that are both proximal and distal from the rotating contact ring 775. By the means, the chamber 790 in which the spring-loaded ball contacts 780a and 780b engage the contact ring 775 will remain fluid-tight.

Now turning to FIGS. 27-30, another variation of an arthroscopic tool 800 is shown which again has a proximal hub 802 coupled to an elongated shaft assembly 805 that extends about central longitudinal axis 806. The shaft assembly 805 includes an outer sleeve 810 with bore 812 and a co-axial inner sleeve assembly 815 that rotates in outer sleeve bore 812 and extends to the working end 818 of the inner sleeve assembly 815. The hub 802 again is adapted for coupling to a handpiece and motor drive controlled by a controller 420A, RF source 420B and negative pressure source 420C as described previously. The controller 420A again includes algorithms for rotating the inner sleeve assembly 815 at selected RPMs as well as for stopping the inner sleeve 815 in a selected rotational position relative to the outer sleeve 810.

In this variation, referring to FIG. 28B, the bore 812 of the outer sleeve 810 extends to a distal open end or opening 820 that includes teeth or serrations 822 along lateral edges of the opening. Referring to FIG. 28A, the inner sleeve assembly 815 extends to its working end 818 which in part comprises a cutter or burr 825 with sharp edges 826 adapted for cutting hard tissue. The plurality of cutting edges 826 can range in number from 2 to 20, and often the burr 825 from 2 to 8 cutting edges. The working end 818 further includes a cutting window 828 with sharp cutting edges that include teeth 830 (see FIG. 29B).

Figure 29A:
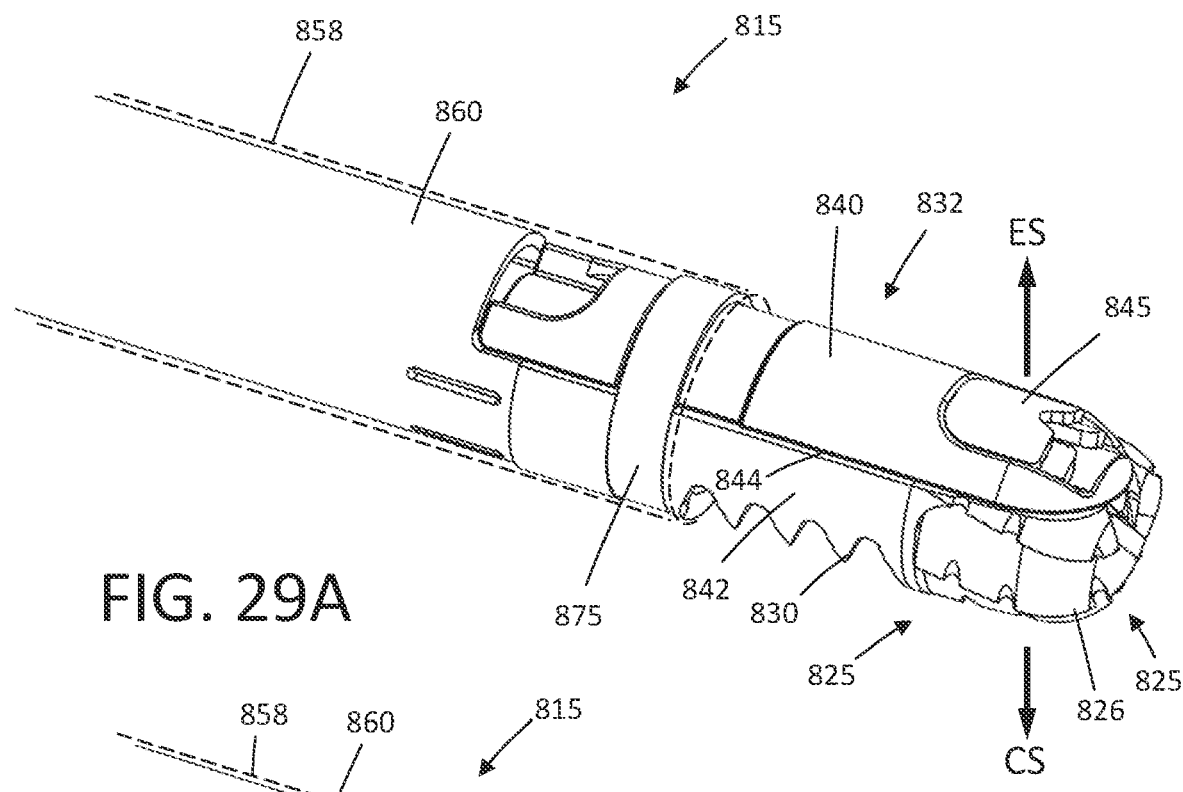
FIG. 29A is a perspective view of the inner sleeve assembly of FIG. 27 with the electrode side of the burr in a upward-facing orientation.
Figure 29B:
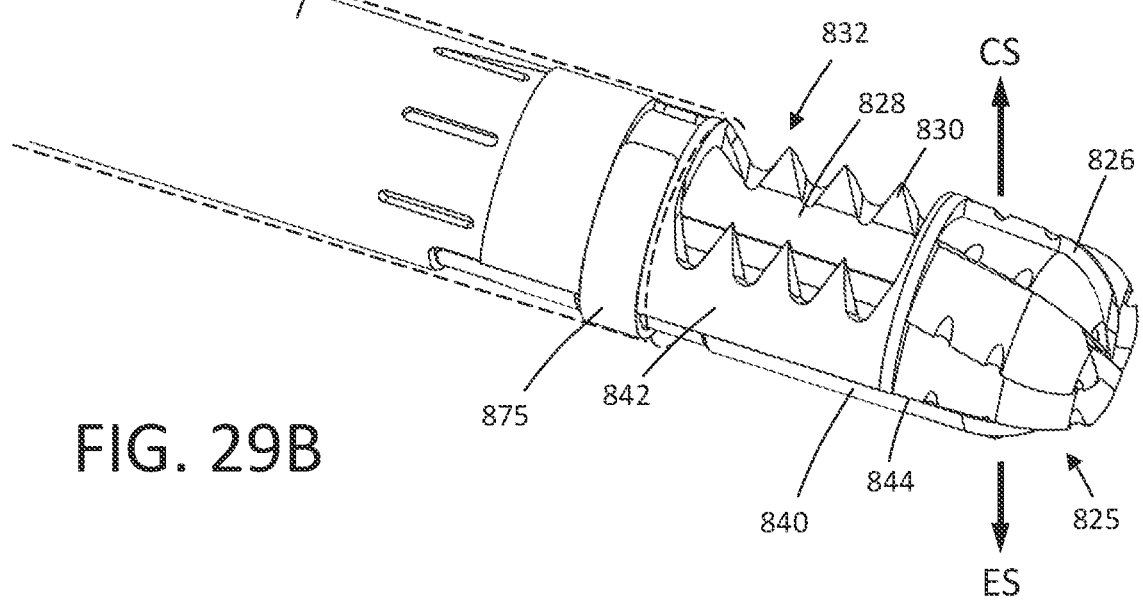
FIG. 29B is a perspective view of the inner sleeve assembly of FIG. 29A with the electrode side of the burr in a downward-facing orientation with a cutting window facing upward.

The working end 818 and burr 825 as can be seen in FIGS. 28B, 29A and 29B is similar to the distal end portion 430 of the inner sleeve assembly 415 of FIGS. 10-15 in that the distal end 818 and burr 825 comprise a housing 832 that is a combination of a longitudinal ceramic or dielectric member 840 coupled to a longitudinal conductive metal member 842 that carries the sharp edges 826. The dielectric member 840 can be a suitable ceramic or glass material and the longitudinal conductive metal member 842 typically is stainless steel. When assembled, the dielectric member 840 and longitudinal metal member 842 have outer surfaces that contact one another along interface 844 which is described in more detail below.

Referring again to FIGS. 28A and 29A, the longitudinal ceramic member 840 carries an active electrode 845 in its outer surface, which may be termed a first polarity electrode herein. For convenience, the side of the distal end 818 that carries electrode 845 is called the electrode side ES and the opposing side configured with window 828 and cutting edges 826 is called the cutting side CS.

Figure 27:
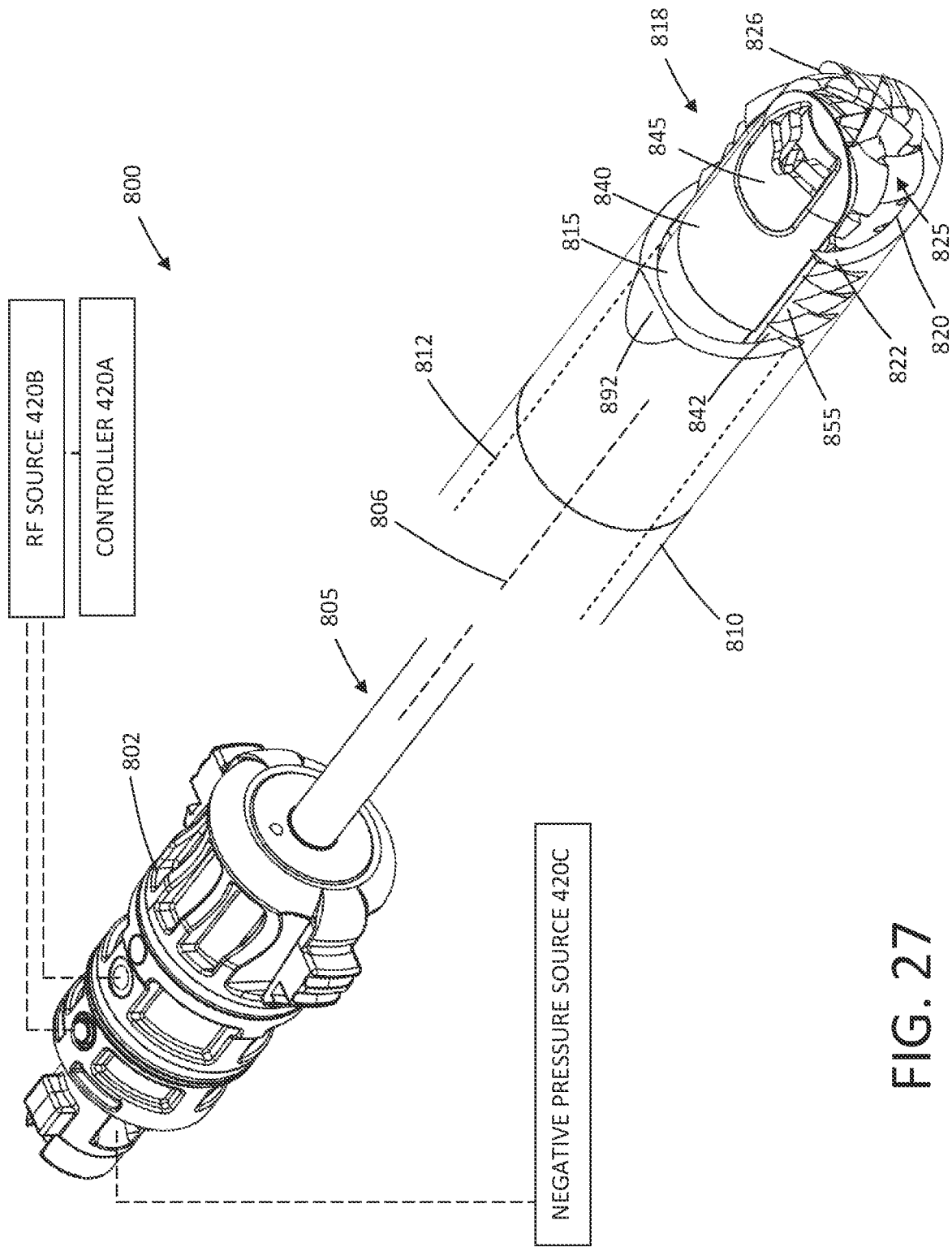
FIG. 27 is a perspective view of another variation of a probe somewhat similar to that of FIG. 10 but having a burr configuration for cutting hard tissue such as bone.

As can be best understood from FIG. 28A, the longitudinal conductive metal member 842 comprises a return electrode 855 (which may be termed a second polarity electrode herein) which cooperates with the first polarity or active electrode 845 to deliver energy to tissue. The active and return electrodes 845 and 855 are operatively coupled to RF source 420B and controller 420A as described above. Referring to FIGS. 27 and 28B, the outer sleeve 810 comprises a conductive metal such as stainless steel with bore 812 therein that extends proximally to the hub 802 and distally to the distal end opening 820. In FIG. 28A, it can be seen that the inner sleeve assembly 815 comprises a co-axial conductive metal inner tubular member 860 that extends proximally to hub 802 (FIG. 27) and extends distally to couple to the burr 825 or housing 832 which consists of the longitudinal dielectric member 840 and the longitudinal metal member 842. A heat shrink material 858 such as FEP is disposed over the inner sleeve and collar 875 described below (FIG. 29A). The metal inner tubular sleeve 860 rotates in bore 812 of the outer sleeve 810.

Figure 30:
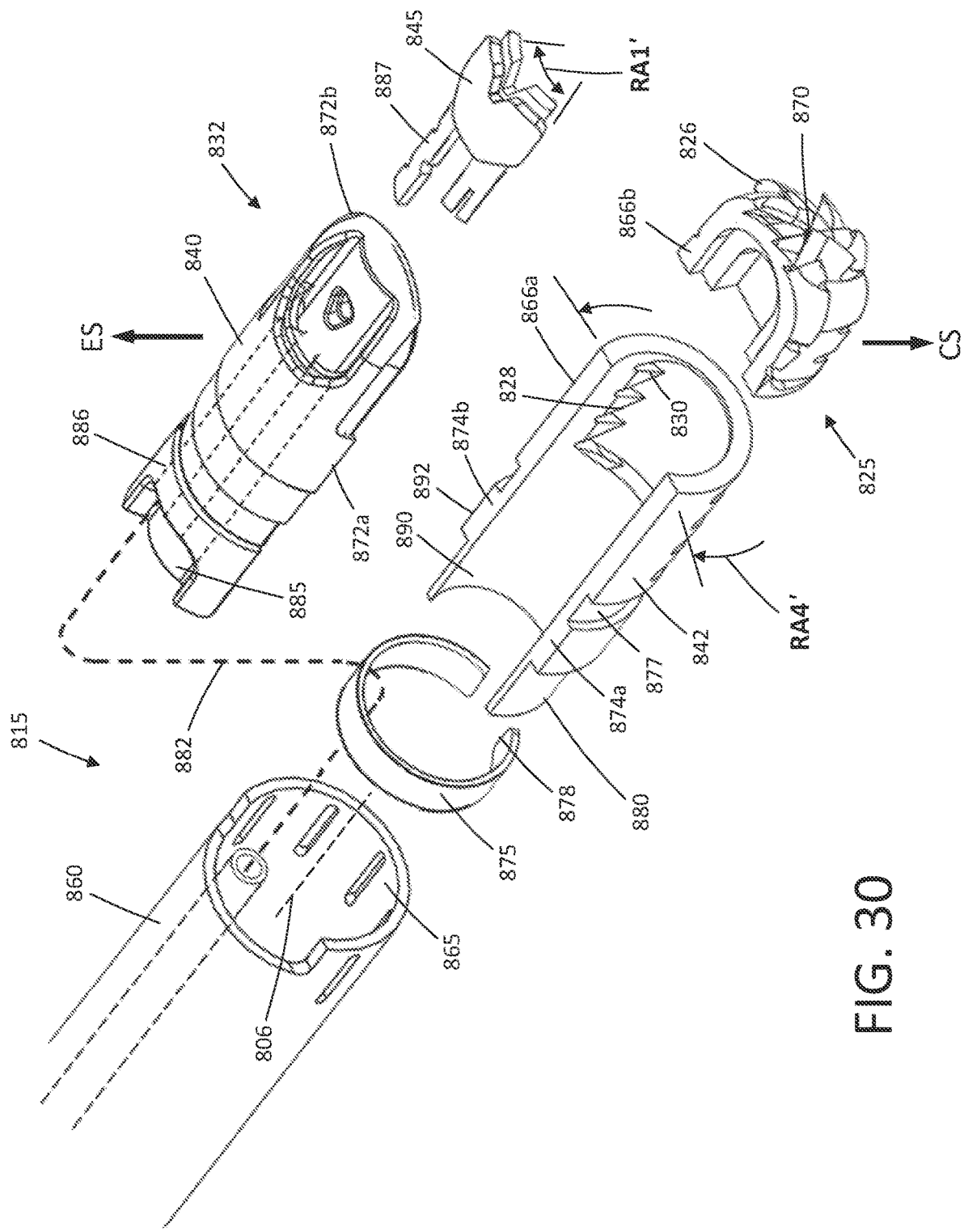
FIG. 30 is a perspective exploded view of the working end of the inner sleeve assembly of FIG. 28A showing the components thereof.

Now turning to FIG. 30, the inner sleeve assembly 815 is shown in exploded view separated from outer sleeve 810 with the electrode side ES facing upward and the cutting side CS facing downward. In FIG. 30, it can be seen that the longitudinal metal member 842 comprises a body that circumferentially extends greater than 180° around axis 806 and interior passageway 865 such that the metal member 842 provides the burr 825 with sufficient strength for cutting hard tissue at high RPMs. In this variation, the longitudinal metal member 842 is fabricated by welding together a proximal element 866a and a distal burr element 866b. The cutting edges 826 extend longitudinally over the length of the burr 825 and distally around distal tip 870 thereof (see also FIGS. 29A and 29B). As can be understood, the longitudinal dielectric member 840 is thus protected from high stresses on the burr cutting edges 826 and cutting edges of window 828 when cutting tissue such as bone at high RPMs. In this variation, the lateral edges 872a and 872b of the dielectric member 840 interface with the lateral edges 874a and 874b of the metal member 842 and are securely fixed together by a retaining collar 875 that fits tightly over reduced diameter annular portion or notch 877 of the dielectric member 840 and the metal member 842 to securely hold the components together. The metal retaining collar 875 has a discontinuity 878 in its circumference to allow the collar to be tensioned and slipped over the components 840 and 842 and then welded.

Referring to FIG. 30, the proximal reduced diameter portion 880 of the longitudinal metal member 842 is dimensioned for insertion into the bore 865 of the thin wall tubular sleeve 860 to form the structural components of the inner sleeve assembly 815. It can be understood how the tubular sleeve 860 with bore 865 therein slides over and engages the proximal portion 880 to the metal member 842 to provide a durable connection.

Still referring to FIG. 30, the electrical connection to the active electrode 845 can be seen. The electrical lead 882 in phantom view extends to the active electrode 845 through a hypotube 884 which is coupled to the inner wall of the tubular member 860. The electrical lead then can extend through a recess 885 in the dielectric member 842 to a channel 886 in the dielectric member to couple to a leg 887 of the active electrode 845. The proximal end (not shown) of the electrical lead 882 extends into a hub 802 (cf. FIG. 27) as described previously to connect to electrical contacts in a handle which allows for rotation of the inner sleeve assembly 815 and for coupling electrical energy to the electrical lead 882.

Referring to FIG. 30, the longitudinal dielectric member 840 together with the longitudinal metal member 842 form a wall around an interior channel 890 therein that communicates within bore 865 in the inner tubular member 860 and a negative pressure source 420C for aspirating tissue chips and fluid from a working space as is known in the art. In one variation shown in FIG. 30, the metal wall portion 505 (disregarding the opening of window 828 therein) extends radially around axis 806 and the interior channel 890 in a radial angle RA4' of at least 120°, and often will extend radially around the interior channel 890 in a radial angle RA4' of at least 180°. When describing the metal wall portion 892 herein that extends in a radial angle indicated at RA4' in FIG. 30, it is meant to refer to the metal wall in a transverse section which is proximal or distal to window 828, where such a wall portion provides the required hoop strength to the metal member 842. Further, referring to FIGS. 30 and 31, the dome-shaped electrode 845 has a surface that extends radially around the axis 806 in a radial angle RA1' of at least 5° or at least 10°. As described previously, the lateral electrode edges are spaced apart from the closest portion of metal member 842 or the outer sleeve opening 820 (i.e., teeth 822) by a radial angle RA2' of at least 100 (see FIG. 31). In one variation, the radial angle RA1' of the surface of electrode 845 is 78° and minimum distance of lateral edges of electrode 845 from the closest return electrode has a radial angle RA2' of 19.5°.

Figure 31:
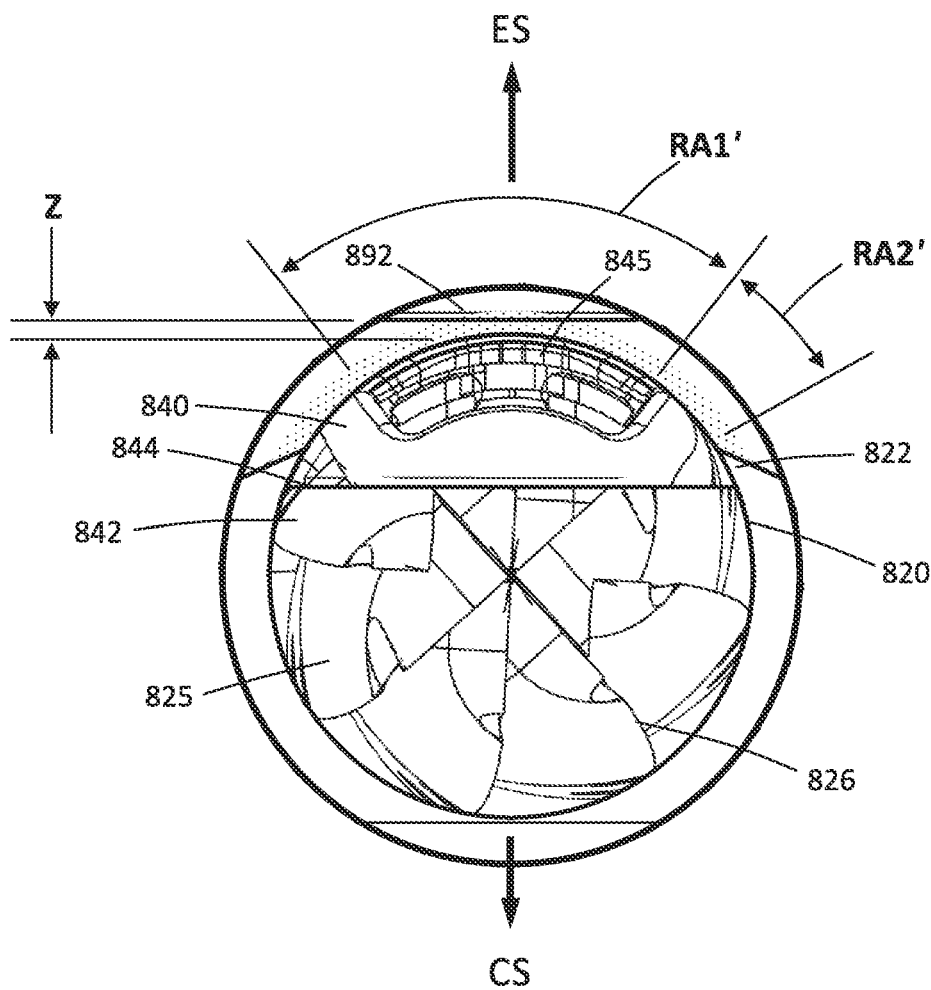
FIG. 31 is an end view the probe of FIG. 27 showing dimensions and arrangements of the components thereof.
Figure 32:
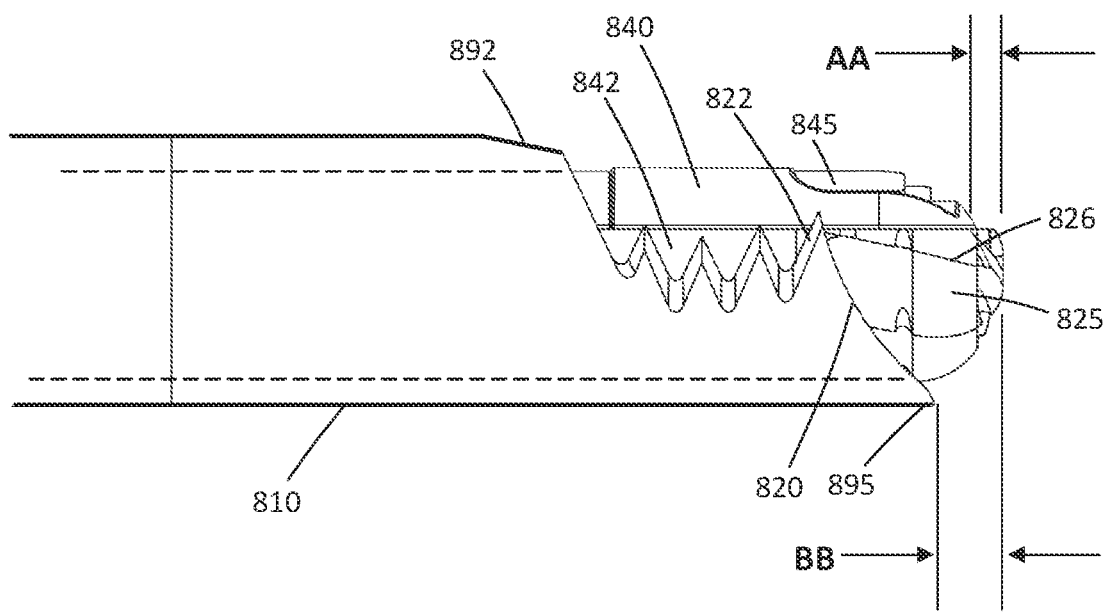
FIG. 32 is a side view of the working end of the probe of FIG. 27 showing dimensions of the components thereof.

Referring to FIGS. 27, 28B and 31, the superior surface of the outer sleeve 810 at the edge of distal opening 820 is configured with a slope or chamfer 892 that allows the working end of the device to be positioned closely to targeted tissue. In one variation, as shown in FIG. 31, the wall thickness Z of the superior wall at the opening edge is less than 50% of the full wall thickness and often less than 40% of the full wall thickness. FIG. 32 is a side view of the working end of the cutting device 800 showing that the distal surfaces of the cutting edges 826 of the burr 825 extend distally beyond the dielectric member 849 by dimension AA which is at least 0.2" or at least 0.03" which protects the ceramic when cutting hard tissue. In one variation, dimension AA is 0.03". FIG. 32 further shows that the distal surfaces of the cutting edges 826 of burr 825 extend distally beyond the distalmost tip 895 of the outer sleeve by dimension BB which is at least 0.05" or at least 0.10" which allows for effective cutting into hard tissue with the tip of the burr 825.

Referring to FIGS. 31 and 32, it can be seen that the outer sleeve 810 and teeth 822 extend around the axis 806 in a radial angle greater that 180° and in one variation the radial angle is greater than 220° at the distalmost teeth 822. As can be understood, during use of the probe, the teeth 822 of the outer sleeve 810 may engage tissue which can tend to flex or flare the teeth 822 outward and away from the rotating inner sleeve assembly 815 which is undesirable as tissue could be trapped between the outer sleeve 810 and the working 818 of the inner sleeve assembly 815. For this reason, at least the distal portion of outer sleeve 810 must be a very hard alloy to resist such flaring or flexing, and has a hardness of at least Rockwell C50 or at least Rockwell C60. In one variation, the material is a 440 stainless steel or a 465SS or a 420SS. In one variation, the diameter of the outer sleeve 810 is 0.210" with a wall thickness of 0.017".

As described in previous embodiments, a stopping mechanism is controlled by the controller 420A that is adapted to stop rotation of inner sleeve assembly 815 in a particular rotational position, for example, with the electrode side ES facing upwardly as in FIG. 27. In general, it can be understood that the devices of the invention described above are adapted to function in two different operational modes. First, the working end of the probe 800 of FIG. 27 utilizes high-speed rotation of the inner sleeve assembly 815 to cut and remove tissue. Second, the controller 420A can stop rotation of the inner sleeve assembly 815 so that the active electrode 845 is exposed and thereafter the electrode arrangement can be energized to coagulate or ablate tissue, depending on wave form and power delivered.

In another aspect of the invention, a third mode of operation is provided and consists of contemporaneous rotation of the inner sleeve assembly 815 together with activation of the active electrode 845. This mode of operation can thereby cut and remove tissue at the same time as coagulating or ablating tissue with RF energy. In this third mode of operation, it is necessary to sequence the activation of RF energy to the active electrode 845 during each 360° rotation of the inner sleeve assembly 815 so that the active electrode 845, effectively, does not form a short circuit with the return electrode 855 of the outer sleeve 810. In one variation, micro-switches can be provided in the proximal hub of the probe to turn RF energy delivery on and off during each rotation of the inner sleeve assembly. However, such micro switches or other similar encoding mechanisms may that operate instantaneously and effectively during high-speed rotation.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. An arthroscopic cutter, comprising:
   an elongated outer sleeve extending about a longitudinal axis with an interior bore having an open distal end;
   an inner sleeve configured to rotate in the interior bore of the elongated outer sleeve, wherein the inner sleeve carries a distal housing including a longitudinal metal member and a longitudinal ceramic member that respectively form a metal longitudinally-extending side wall portion and a ceramic longitudinally-extending side wall portion of the distal housing, the metal longitudinally-extending side wall portion and the ceramic longitudinally-extending side wall portion each forming a respective part of an inner wall surface of the distal housing, the inner wall surface defining an inner channel that extends through the distal housing to communicate with a negative pressure source; and
   an electrode disposed in an outer surface of the longitudinal ceramic member,
   wherein the longitudinal metal member includes: (i) a distal portion with sharp cutting edges extending around sides and a distal tip of the longitudinal metal member; and (ii) a proximal portion with a window therein configured with circumferentially spaced apart lateral window edges adapted for cutting tissue, the distal portion and the proximal portion being separately-formed pieces that are welded together within the distal housing such that the window is spaced apart longitudinally from the sharp cutting edges along the longitudinal metal member,
   wherein the sharp cutting edges of the distal portion of the longitudinal metal member extend distally beyond a distal end of the longitudinal ceramic member and a distalmost end of the elongated outer sleeve,
   wherein a distal end of the longitudinal ceramic member extends distally beyond a distal end of the window.

2. The arthroscopic cutter of claim 1, wherein the window includes at least one window edge that is configured with sharp teeth.

3. The arthroscopic cutter of claim 1, wherein the sharp cutting edges of the distal portion of the longitudinal metal member extend distally at least 1 mm beyond the distalmost end of the elongated outer sleeve.

4. The arthroscopic cutter of claim 1, wherein the sharp cutting edges extending around the sides of the longitudinal metal member extend over a radial angle of at least 120°.

5. The arthroscopic cutter of claim 1, wherein the electrode includes an outer surface extending over a radial angle of at least 5° or at least 10°.

6. The arthroscopic cutter of claim 1, wherein the electrode includes lateral electrode edges that are spaced apart from the closest portion of the longitudinal metal member by a radial angle of at least 10°.

7. The arthroscopic cutter of claim 1, wherein the electrode includes lateral electrode edges that are spaced apart from the closest portion of the elongated outer sleeve by a radial angle of at least 10°.

8. The arthroscopic cutter of claim 5, wherein the outer surface of the electrode is non-planar.

9. The arthroscopic cutter of claim 5, wherein the outer surface of the electrode defines a radius.

10. The arthroscopic cutter of claim 9, wherein the radius of the outer surface of the electrode is similar to an outer radius of the longitudinal ceramic member.

11. An arthroscopic cutter, comprising:
    an elongated outer sleeve extending about a longitudinal axis with an interior bore having an open termination in a distal end of the elongated outer sleeve;
    an inner sleeve configured to rotate in the interior bore of the elongated outer sleeve, wherein the inner sleeve carries a distal housing including a longitudinal metal member and a longitudinal ceramic member that respectively form a metal longitudinally-extending side wall portion and a ceramic longitudinally-extending side wall portion of the distal housing, the metal longitudinally-extending side wall portion and the ceramic longitudinally-extending side wall portion each forming a respective part of an inner wall surface of the distal housing, the inner wall surface defining an inner channel that extends through the distal housing to communicate with a negative pressure source, wherein the longitudinal metal member comprises a return electrode and includes a proximal portion with a window therein configured with circumferentially spaced apart lateral window edges adapted for cutting tissue, wherein the longitudinal metal member includes a distal portion with sharp cutting edges, wherein the sharp cutting edges of the distal portion of the longitudinal metal member are spaced apart longitudinally from the window along the longitudinal metal member and extend distally beyond a distal end of the longitudinal ceramic member; and an active electrode disposed in an outer surface of the longitudinal ceramic member, wherein the proximal portion and the distal portion of the longitudinal metal member are separately-formed pieces that are welded together within the distal housing.

12. The arthroscopic cutter of claim 11, wherein the sharp cutting edges of the distal portion of the longitudinal metal member extend around sides and a distal tip of the longitudinal metal member.

13. An arthroscopic cutter, comprising:

an elongated outer sleeve extending about a longitudinal axis with an interior bore having an open termination in a distal end of the elongated outer sleeve;

an inner sleeve configured to rotate in the interior bore of the elongated outer sleeve, wherein the inner sleeve carries a distal housing including a longitudinal metal member and a longitudinal ceramic member that respectively form a metal longitudinally-extending side wall portion and a ceramic longitudinally-extending side wall portion of the distal housing, the metal longitudinally-extending side wall portion and the ceramic longitudinally-extending side wall portion each forming a respective part of an inner wall surface of the distal housing, the inner wall surface defining an inner channel that extends through the distal housing to communicate with a negative pressure source, wherein the longitudinal metal member comprises a return electrode and includes a proximal portion with a window therein configured with circumferentially spaced apart lateral window edges adapted for cutting tissue, wherein the longitudinal metal member includes a distal portion with sharp cutting edges, wherein the sharp cutting edges of the distal portion of the longitudinal metal member are spaced apart longitudinally from the window along the longitudinal metal member and extend distally beyond a distal end of the longitudinal ceramic member; and an active electrode disposed in an outer surface of the longitudinal ceramic member, wherein a distal end of the longitudinal ceramic member extends distally beyond a distal end of the window.

14. The arthroscopic cutter of claim 13, wherein the sharp cutting edges of the distal portion of the longitudinal metal member extend distally beyond a distalmost end of the elongated outer sleeve.

15. The arthroscopic cutter of claim 13, wherein the sharp cutting edges of the distal portion of the longitudinal metal member extend around sides and a distal tip of the longitudinal metal member.

16. The arthroscopic cutter of claim 13, wherein the proximal portion and the distal portion of the longitudinal metal member are separately-formed pieces that are welded together within the distal housing.

17. The arthroscopic cutter of claim 14, wherein the sharp cutting edges of the distal portion of the longitudinal metal member extend distally at least 1 mm beyond the distalmost end of the elongated outer sleeve.

18. The arthroscopic cutter of claim 13, wherein the sharp cutting edges extend around sides of the longitudinal metal member over a radial angle of at least 120°.

19. The arthroscopic cutter of claim 13, wherein the active electrode includes an outer surface extending over a radial angle of at least 5° or at least 10°.

20. The arthroscopic cutter of claim 13, wherein the active electrode includes lateral electrode edges that are spaced apart from the closest portion of the longitudinal metal member by a radial angle of at least 10°.

* * * * *